(12) United States Patent
Alberici et al.

(10) Patent No.: US 9,676,847 B2
(45) Date of Patent: Jun. 13, 2017

(54) IL-17 ANTAGONIST ANTIBODIES

(71) Applicant: Orega Biotech, Ecully (FR)

(72) Inventors: Gilles Alberici, Grezieu la Varenne (FR); Jeremy Bastid, Craponne (FR); Armand Bensussan, Paris (FR); Nathalie Bonnefoy, Lyons (FR); Jean-Francois Eliaou, Montpellier (FR)

(73) Assignee: Orega Biotech, Ecully (FR)

( * ) Notice: Subject to any disclaimer, the term of this patent is extended or adjusted under 35 U.S.C. 154(b) by 0 days.

(21) Appl. No.: 14/396,689

(22) PCT Filed: Jun. 25, 2013

(86) PCT No.: PCT/EP2013/063328
§ 371 (c)(1),
(2) Date: Oct. 23, 2014

(87) PCT Pub. No.: WO2014/001368
PCT Pub. Date: Jan. 3, 2014

(65) Prior Publication Data
US 2015/0104457 A1   Apr. 16, 2015

Related U.S. Application Data

(60) Provisional application No. 61/663,935, filed on Jun. 25, 2012.

(51) Int. Cl.
| | |
|---|---|
| *C07K 16/24* | (2006.01) |
| *A61K 39/395* | (2006.01) |
| *C12P 21/00* | (2006.01) |
| *C12P 21/02* | (2006.01) |
| *G01N 33/574* | (2006.01) |
| *G01N 33/68* | (2006.01) |
| *C12N 15/09* | (2006.01) |
| *C12N 15/12* | (2006.01) |
| *A61K 39/00* | (2006.01) |

(52) U.S. Cl.
CPC ......... *C07K 16/244* (2013.01); *A61K 39/395* (2013.01); *C12P 21/00* (2013.01); *C12P 21/02* (2013.01); *G01N 33/57415* (2013.01); *G01N 33/6869* (2013.01); *A61K 2039/505* (2013.01); *C07K 2317/21* (2013.01); *C07K 2317/24* (2013.01); *C07K 2317/33* (2013.01); *C07K 2317/34* (2013.01); *C07K 2317/54* (2013.01); *C07K 2317/55* (2013.01); *C07K 2317/56* (2013.01); *C07K 2317/622* (2013.01); *C07K 2317/624* (2013.01); *C07K 2317/626* (2013.01); *C07K 2317/76* (2013.01); *C07K 2317/92* (2013.01); *C12N 15/09* (2013.01)

(58) Field of Classification Search
None
See application file for complete search history.

(56) References Cited

U.S. PATENT DOCUMENTS 6,274,711 B1 * 8/2001 Golstein ............... C07K 14/52
435/975

FOREIGN PATENT DOCUMENTS

| WO | WO-2006054059 A1 | 5/2006 |
| WO | WO 2007/149032 | * 12/2007 |
| WO | WO-2009136286 A2 | 11/2009 |
| WO | WO-2011053763 A2 | 5/2011 |
| WO | WO-2011141823 A2 | 11/2011 |

OTHER PUBLICATIONS

European Patent Office International Search Report and Written Opinion of the International Searching Authority for PCT/EP2013/063328 mailed Sep. 11, 2013 (16 pages).
European Patent Office International Preliminary Report on Patentability for PCT/EP2013/063328 mailed Jul. 4, 2014 (16 pages).
Iwakura, Yoichiro et al., "Functional Specialization of Interleukin-17 Family Members," 2011 Immunity, vol. 34, pp. 149-162.
Gaffen, Sarah L., "Biology of recently discovered cytokines: Interleukin-17—a unique inflammatory cytokine with roles in bone biology and arthritis," 2004 Arthritis Res Ther, vol. 6, pp. 240-247.
Gaffen, Sarah L., "Structure and signalling in the IL-17 receptor superfamily," 2009 Nat Rev Immunol., vol. 9, No. 8 (24 pages).
Gaffen, SL, "Structure and signalling in the IL-17 receptor family," 2009 Erratum in Nat Rev Immunol., vol. 9, No. 10, p. 747.
Prabhala, Rao H., "Elevated IL-17 produced by $T_H17$ cells promotes myeloma cell growth and inhibits immune function in multiple myeloma," 2010 Blood vol. 115, No. 26, pp. 5385-5392.
Zhu, Xingwu, et al., "IL-17 expression by breast-cancer-associated macrophages: IL-17 promotes invasiveness of breast cancer cell lines," 2008 Breast Cancer Research, vol. 10 (11 pages).
Ji, Yuqiang et al., "Th17 cells: positive or negative role in tumor?," 2010 Cancer Immunol Immunother, vol. 59, No. 7, pp. 979-987.
Zhang, Jing-Ping et al., "Increased intratumoral IL-17 producing cells correlate with poor survival in hepatocellular carcinoma patients," 2009 J Hepatol, vol. 50, No. 5, pp. 980-989.

* cited by examiner

*Primary Examiner* — Bridget E Bunner
*Assistant Examiner* — Fozia Hamud
(74) *Attorney, Agent, or Firm* — Harris Beach PLLC

(57) ABSTRACT

The disclosure relates to antibodies against human IL-17 which act as antagonists of IL-17, and their use in the diagnosis or treatment of IL-17 mediated diseases.

33 Claims, 1 Drawing Sheet

IL-17 ANTAGONIST ANTIBODIES

CROSS-REFERENCE TO RELATED APPLICATIONS

This application is a national stage application under 35 U.S.C. §371 of PCT Application No. PCT/EP2013/063328, filed Jun. 25, 2013, which claims priority to and the benefit of U.S. Provisional Application No. 61/663,935, filed Jun. 25, 2012, which is incorporated herein by reference in its entirety.

BACKGROUND OF THE INVENTION

Field of the Invention

The invention relates generally to novel IL-17 antagonist antibodies and their use in the diagnosis or treatment of IL-17 mediated diseases.

Background

Interleukin-17 ("IL-17"), also known as IL-17A and CTLA-8, is a pro-inflammatory cytokine that stimulates secretion of various other cytokines in a variety of cell types. For example, IL-17 can induce IL-6, IL-8, G-CSF, TNF-α, IL-1β, and IFN-γ, as well as numerous chemokines and other effectors. See, e.g., Gaffen, S. L., *Arthritis Research & Therapy* 6: 240-247 (2004).

IL-17 is expressed by $T_H17$ cells, which are involved in the pathology of inflammation and autoimmunity. It is also expressed by CD8+ T cells, γδ cells, NK cells, NKT cells, macrophages and dendritic cells. IL-17 and Th17 are linked to pathogenesis of diverse autoimmune and inflammatory diseases, but are essential to host defense against many microbes, particularly extracellular bacteria and fungi. IL-17 can form homodimers or heterodimers with its family member, IL-17F. IL-17 binds to both IL-17 RA and IL-17 RC to mediate signaling. IL-17, signaling through its receptor, activates the NF-κB transcription factor, as well as various MAPKs. See, e.g., Gaffen, S., *Nature Rev. Immunol.* 9: 556-567 (2009).

IL-17 can act in cooperation with other inflammatory cytokines such as TNF-α, IFN-γ, and IL-1β to mediate pro-inflammatory effects. See, e.g., Gaffen, S. L., *Arthritis Research & Therapy* 6: 240-247 (2004). Increased levels of IL-17 have been implicated in numerous diseases, including rheumatoid arthritis (RA), Systemic Lupus Erythematosus (SLE), bone erosion, intraperitoneal abscesses, inflammatory bowel disease, Crohn's diseases, allograft rejection, psoriasis, angiogenesis, atheroscloerosis, and multiple sclerosis. See, e.g., Gaffen, S. L., *Arthritis Research & Therapy* 6: 240-247 (2004); US Publ. No. 2008/-0269467 A1, published Oct. 30, 2008; Iwakura, Y., H. Ishigame, et al. (2011) "Functional specialization of interleukin-17 family members" *Immunity* 34(2): 149-162.

IL-17 and IL-17-producing $T_H17$ cells have recently been implicated in certain cancers, Ji and Zhang, *Cancer Immunol Immunother* 59: 979-987 (2010). For example, IL-17-expressing $T_H17$ cells were shown to be involved in multiple myeloma, Prabhala et al., *Blood*, online DOI 10.1182/blood-2009-10-246660, Apr. 15, 2010, and to correlate with poor prognosis in patients with HCC, Zhang et al., *J. Hepatology* 50: 980-89 (2009). Also, IL-17 was found to be expressed by breast-cancer-associated macrophages, Zhu et al., *Breast Cancer Research* 10:R95 (2008). More recently, the inventors showed that IL-17 antibodies are able to act on primary tumors and metastases in various kinds of cancer (see WO 2011/141823).

Accordingly, antibodies against IL-17 are useful tools for the diagnosis and/or treatment of a large panel of diseases. Novel antibodies against IL-17 with specific and advantageous properties are therefore required.

SUMMARY OF THE INVENTION

The present invention relates to novel isolated IL-17 antibodies.

The invention also relates to antibodies which comprise a variable light chain (VL) comprising the CDRs of the VL chain of said antibodies and a variable heavy chain (VH) comprising the CDRs of the VH chain of said antibodies, respectively.

The invention also relates to the use of said antibodies in the diagnosis, prevention or treatment of IL-17 mediated diseases and disorders.

According to one aspect, the present invention relates to an isolated IL-17 antibody comprising a VH region comprising the amino acid sequence as set forth in SEQ ID NO: 3 and/or a VL region comprising the amino acid sequence as set forth in SEQ ID NO: 4.

According to another aspect, the present invention relates to an isolated IL-17 antibody which comprises a VH chain comprising the amino acid sequence as set forth in SEQ ID NO: 5 and/or a VL chain comprising the amino acid sequence as set forth in SEQ ID NO: 4.

According to another aspect, the present invention relates to an isolated IL-17 antibody which comprises a VH chain comprising the amino acid sequence as set forth in SEQ ID NO: 6 and/or a VL chain comprising the amino acid sequence as set forth in SEQ ID NO: 7.

According to another aspect, the present invention relates to an isolated IL-17 antibody which binds an epitope comprising a sequence of the human IL-17A as set forth in SEQ ID NO: 8 and/or SEQ ID NO: 9.

According to another aspect, the present invention relates to an isolated antibody that specifically binds to the same IL-17 epitope as reference monoclonal antibody OREG-203, OREG-207 or OREG-210.

According to another aspect, the present invention relates to an isolated antibody that specifically binds to IL-17, wherein said antibody competitively inhibits reference monoclonal antibody OREG-203, OREG-207 or OREG-210 from specifically binding to IL-17.

According to another aspect, the present invention relates to an isolated antibody that specifically binds to IL-17, wherein said antibody is monoclonal antibody OREG-203, OREG-207 or OREG-210.

According to another aspect, the present invention relates to an isolated antibody that specifically binds to IL-17, wherein the VH of said antibody comprises a Kabat heavy chain complementarity determining region-1 (VH-CDR1) amino acid sequence which is identical, or identical except for conservative amino acid substitutions, to SEQ ID NO: 15 or SEQ ID NO: 21, advantageously wherein said VH-CDR1 amino acid sequence is SEQ ID NO: 15 or SEQ ID NO: 21.

According to another aspect, the present invention relates to an isolated antibody that specifically binds to IL-17, wherein the VH of said antibody comprises a Kabat heavy chain complementarity determining region-2 (VH-CDR2) amino acid sequence which is identical, or identical except for conservative amino acid substitutions, to SEQ ID NO: 16 or SEQ ID NO: 22, advantageously wherein said VH-CDR2 amino acid sequence is SEQ ID NO: 16 or SEQ ID NO: 22.

According to another aspect, the present invention relates to an isolated antibody that specifically binds to IL-17, wherein the VH of said antibody comprises a Kabat heavy chain complementarity determining region-3 (VH-CDR3) amino acid which is sequence identical, or identical except for conservative amino acid substitutions, to SEQ ID NO: 17 or SEQ ID NO: 23, advantageously wherein said VH-CDR3 amino acid sequence is SEQ ID NO: 17 or SEQ ID NO: 23.

According to another aspect, the present invention relates to an isolated antibody that specifically binds to IL-17, wherein the VL of said antibody comprises a Kabat light chain complementarity determining region-1 (VL-CDR1) amino acid sequence which is identical, or identical except for conservative amino acid substitutions, to SEQ ID NO: 18 or SEQ ID NO: 24, advantageously wherein said VL-CDR1 amino acid sequence is SEQ ID NO: 18 or SEQ ID NO: 24.

According to another aspect, the present invention relates to an isolated antibody that specifically binds to IL-17, wherein the VL of said antibody comprises a Kabat light chain complementarity determining region-2 (VL-CDR2) amino acid sequence which is identical, or identical except for conservative amino acid substitutions, to SEQ ID NO: 19 or SEQ ID NO: 25, advantageously wherein said VL-CDR2 amino acid sequence is SEQ ID NO: 19 or SEQ ID NO: 25.

According to another aspect, the present invention relates to an isolated antibody that specifically binds to IL-17, wherein the VL of said antibody comprises a Kabat light chain complementarity determining region-3 (VL-CDR3) amino acid sequence which is identical, or identical except for conservative amino acid substitutions, to SEQ ID NO: 20 or SEQ ID NO: 26, advantageously wherein said VL-CDR3 amino acid sequence is SEQ ID NO: 20 or SEQ ID NO: 26.

According to another aspect, the present invention relates to an isolated antibody that specifically binds to IL-17, wherein the VH of said antibody comprises VH-CDR1, VH-CDR2, and VH-CDR3 amino acid sequences comprising:
  a) SEQ ID NOs: 15, 16 and 17, respectively;
  b) SEQ ID NOs: 21, 22, and 23, respectively;
  c) SEQ ID NOs: 15, 16 and 17, respectively, except for conservative amino acid substitutions in one or more of said VH-CDRs; or
  d) SEQ ID NOs: 21, 22, and 23, respectively, except for conservative amino acid substitutions in one or more of said VH-CDRs.

According to another aspect, the present invention relates to an isolated antibody that specifically binds to IL-17, wherein the VL of said antibody or fragment thereof comprises VL-CDR1, VL-CDR2, and VL-CDR3 amino acid sequences comprising:
  a) SEQ ID NOs: 18, 19 and 20, respectively;
  b) SEQ ID NOs: 24, 25 and 26, respectively;
  c) SEQ ID NOs: 18, 19 and 20, respectively, except for conservative amino acid substitutions in one or more of said VL-CDRs; or
  d) SEQ ID NOs: 24, 25 and 26, respectively, except for conservative amino acid substitutions in one or more of said VL-CDRs.

In an embodiment, the antibody of the invention comprises a light chain constant region selected from the group consisting of a human kappa constant region and a human lambda constant region.

In another embodiment, the antibody of the invention comprises a heavy chain constant region or fragment thereof, advantageously human IgG1, IgG2, IgG3, IgG4, IgM, IgA1, IgA2, IgE or IgD.

In another embodiment, the antibody of the invention is a chimeric antibody.

In another embodiment, the antibody of the invention is a human or humanized antibody.

In another embodiment, the antibody of the invention is a monoclonal antibody.

In another embodiment, the antibody of the invention is an antagonist of IL-17, advantageously an antagonist of an human IL-17 polypeptide.

In another embodiment, the antibody of the invention has neutralizing activity against IL-17.

In another embodiment, the antibody of the invention is an antibody fragment directed against IL-17, advantageously selected from the group consisting of Fv, Fab, F(ab')2, Fab', dsFv, scFv, sc(Fv)2 and diabodies.

The invention also relates to an isolated nucleic acid comprising a sequence encoding the antibody of the invention, or a composition comprising an isolated nucleic acid sequence encoding a VL region and an isolated nucleic acid encoding a VH region of the antibody of the invention, or a vector comprising said isolated nucleic acid or a host cell comprising said isolated nucleic acid sequence or said vector.

The invention also relates to a pharmaceutical composition comprising the antibody of the invention and a pharmaceutically acceptable carrier.

The invention also relates to the antibody or the pharmaceutical composition of the invention for its use in diagnosis and therapy.

The invention also relates to a kit comprising the antibody of the invention.

The invention also relates to a method of treating a disease treatable by neutralization of IL-17, the method comprising administering to a subject an effective amount of the antibody or the pharmaceutical composition of the invention. Said disease is advantageously selected from the group consisting of an autoimmune disease, a chronic inflammatory disease and cancer.

The invention also relates to a method of producing an antibody that specifically binds IL-17, comprising culturing the host cell of the invention under conditions suitable for expressing said antibody, and recovering said antibody.

DETAILED DESCRIPTION OF THE INVENTION

Definitions:

The term "IL-17" denotes the IL-17 protein also named as IL-17A and CTLA-8. The sequence of the human IL-17A is as set forth in SEQ ID NO: 1. The sequence of the human IL-17F is as set forth in SEQ ID NO: 2.

The term "IL-17 antibody" refers to an antibody directed against human IL-17.

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hyper variable or complementarity determining regions (CDRs). Occasionally, residues from non hyper variable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs. This particular region has been described by Kabat et al. (1983) U.S. Dept. of Health and Human Services, "Sequences of Proteins of Immunological Interest" and by Chothia and Lesk, *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an IL-17 antibody or antigen-binding fragment, variant, or derivative thereof of the present invention are according to the Kabat numbering system. It is noted that sequences presented in the accompanying SEQUENCE LISTING are not numbered according to Kabat, but it is well within the ordinary skill in the art to determine the Kabat numbering of sequences in the SEQUENCE LISTING.

The term "chimeric antibody" refers to an antibody which comprises a VH domain and a VL domain of an antibody derived from the isolated murine antibody, and a CH domain and a CL domain of a human antibody.

According to the invention, the term "humanized antibody" refers to an antibody having variable region framework and constant regions from a human antibody (e.g., an "acceptor" antibody) but retains the CDRs and optionally, select framework residues of the isolated murine antibody (e.g., the "parent" antibody).

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "purified" and "isolated" it is meant, when referring to a polypeptide (i.e. an antibody according to the invention) or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

Antibodies and Polypeptides of the Invention:

The present invention provides for isolated antibodies or fragments thereof that are directed against human IL-17. In particular, the inventors have isolated three antibodies named OREG-203, OREG-207 and OREG-210.

One aspect of the invention thus relates to a murine IL-17 antibody, namely OREG-203, OREG-207 or OREG-210.

In another embodiment, the antibody of the invention comprises a variable light chain (VL) comprising the CDRs of the VL chain of the OREG-203, OREG-207 or OREG-210 antibody, and/or a variable heavy chain (VH) comprising the CDRs of the VH chain of the OREG-203, OREG-207 or OREG-210 antibody.

In another embodiment the antibody of the invention comprises the VL chain of the OREG-203, OREG-207 or OREG-210 antibody, and/or the VH chain of the OREG-203, OREG-207 or OREG-210 antibody.

The inventors have cloned and characterized the variable domain of the light and heavy chains of these 3 antibodies (OREG-203, OREG-207 and OREG-210), which all act as neutralizing antibody or antagonist of IL-17. The corresponding sequences are shown in Table 2.

TABLE 2

VH and VL domains of mAbs OREG-203, OREG-207 and OREG-210:

| MAb Domains | |
|---|---|
| VH of Ab OREG-203 | MAWISIILFLVATAIGVHSQAQLQQSGAELVKPGASVKM SCKAFGYTFTTFPIEWMKQNHGKSLEWIGNFHPYNDYTK YNEKFKGKAKLTVEKSSRTVYLELSRLTSDDSAVYYCAR GAYYGDYVSHTMDFWGQGTSVTVSS (SEQ ID NO: 3) |
| VL of Ab OREG-203 | METDTLLLWVLLLWVPGSTGNIVLTQSPASLAVSLGQRA TISCRASESVDSYGNSFMHWYQQKPGQPPKLLIYLASNL ESGVPARFSGSGSRTDFTLTIDPVEADDAAIYYCQQNNE DPLTFGAGTKLELK (SEQ ID NO: 4) |
| VH of Ab OREG-207 | MAWISIILFLVATAIGVHSQAQLQQSGAELVKPGASVKM SCKAFGYTFTTFPIEWMKQNHGKSLEWIGNFHPYNDYTK YNEKFKGKAKLTVEKSSSTVYLELSRLTSDDSAVYYCAR GAYYGDYVSHTMDFWGQGTSVTVSS (SEQ ID NO: 5) |
| VL of Ab OREG-207 | METDTLLLWVLLLWVPGSTGNIVLTQSPASLAVSLGQRA TISCRASESVDSYGNSFMHWYQQKPGQPPKLLIYLASNL ESGVPARFSGSGSRTDFTLTIDPVEADDAAIYYCQQNNE DPLTFGAGTKLELK (SEQ ID NO: 4) |
| VH of Ab OREG-210 | MAVLGLLLCLVTFPSCVLSQVQLKESGPDLVAPSQSLSI TCTVSGFSLTSYGIHWVRQPPGKGLEWLVVIWSDGTTTY NSALKSRLSISKDNSKSQVFLKMNSLQTDDTAMYYCASS YDYLYHYTMDYWGQGTSVTVSS (SEQ ID NO: 6) |
| VL of Ab OREG-210 | MKLPVRLLVLMFWIPASSSDVVMTQTPLSLPVSLGDQAS ISCRSSQSLVHSNGNTYFHWYLQKPGQSPKLLIYKVSNR FSGVPDRFSGSGSGTDFTLKISRVEAEDLGVYFCSQSTH VPLTFGAGTNLELK (SEQ ID NO: 7) |

The sequence underlined corresponds to the leading sequence.

The Kabat CDRs of Ab OREG-203 and OREG-207 are identical and have the following amino acid sequences:

VH-CDR1

(SEQ ID NO: 15)

TFPIE

VH-CDR2

(SEQ ID NO: 16)

NFHPYNDYTKYNEKFKG

VH-CDR3

(SEQ ID NO: 17)

GAYYGDYVSHTMDFWGQGTSVTVSS

VL-CDR1

(SEQ ID NO: 18)

RASESVDSYGNSFMH

VL-CDR2

(SEQ ID NO: 19)

LASNLES

VL-CDR3

(SEQ ID NO: 20)

QQNNEDPLTFGAGTKLELK

The Kabat CDRs of Ab OREG-210 have the following amino acid sequences:

VH-CDR1

(SEQ ID NO: 21)

SYGIH

VH-CDR2

(SEQ ID NO: 22)

VIWSDGTTTYNSALKS

VH-CDR3

(SEQ ID NO: 23)

SYDYLYHYTMDYWGQGTSVTVSS

VL-CDR1

(SEQ ID NO: 24)

RSSQSLVHSNGNTYFH

VL-CDR2

(SEQ ID NO: 25)

KVSNRFS

VL-CDR3

(SEQ ID NO: 26)

SQSTHVPLTFGAGTNLELK

In certain embodiments, the antibodies according to the invention comprise anti-IL-17 antibodies or antigen-binding fragments, variants, or derivatives thereof that bind to IL-17, e.g., mAbs OREG-203, OREG-207 and OREG-210, as described herein. In certain embodiments the anti-IL-17 antibodies bind human IL-17, especially human IL-17A. In specific embodiments the anti-IL-17 antibodies bind the IL-17A/A homodimer and/or the IL-17A/F heterodimer. In other embodiments, the anti-IL-17 antibodies have a neutralizing effect on the activity of IL-17. In one embodiment, neutralizing activity of the antibody is measured by ability to block secretion of IL-6 in normal human dermal fibroblasts, although other assays known to those of skill in the art could also be used.

In one embodiment, the present invention provides an isolated binding molecule, e.g., an antibody or antigen binding fragment thereof, which specifically binds to the same IL-17 epitope as mAbs OREG-203, OREG-207 and/or OREG-210. In another embodiment, the present invention provides an isolated binding molecule, e.g., an antibody or antigen binding fragment thereof, which specifically binds to IL-17, and competitively inhibits mAbs OREG-203, OREG-207 or OREG-210 from specifically binding to IL-17.

In one embodiment, the present invention provides an isolated antibody or antigen-binding fragment thereof comprising, consisting essentially of, or consisting of an immunoglobulin heavy chain variable domain (VH domain), where at least one of the CDRs of the VH domain has an amino acid sequence that is identical to CDR1, CDR2 or CDR3 of any one of the VH regions represented by SEQ ID NO: 3, SEQ ID NO: 5, or SEQ ID NO: 6.

In another embodiment, the present invention provides an isolated antibody or antigen-binding fragment thereof comprising, consisting essentially of, or consisting of a VH domain that has an amino acid sequence that is identical to SEQ ID NO: 3, SEQ ID NO: 5, or SEQ ID NO: 6, wherein an anti-IL-17 antibody comprising the encoded VH domain specifically or preferentially binds to IL-17, more specifically, human IL-17.

In another embodiment, the present invention provides an isolated antibody or antigen-binding fragment thereof comprising, consisting essentially of, or consisting of an immunoglobulin light chain variable domain (VL domain), where at least one of the CDRs of the VL domain has an amino acid sequence that is identical to CDR1, CDR2 or CDR3 of SEQ ID NO: 4 or SEQ ID NO: 7.

In a further embodiment, the present invention includes an isolated antibody or antigen-binding fragment thereof comprising, consisting essentially of, or consisting of a VL domain that has an amino acid sequence that is identical to SEQ ID NO: 4 or SEQ ID NO: 7, wherein an anti-IL-17 antibody comprising the encoded VL domain specifically or preferentially binds to IL-17.

A further embodiment of the invention relates to an IL-17 antibody comprising:
a heavy chain variable domain that is 80%, 85%, 90%, 91%, 92%, 93%, 94%, 95%, 96%, 97%, 98%, or 99%, identical to a sequence as set forth in SEQ ID NO: 3 and/or a light chain variable domain that is 80%, 85%, 90%, 91%, 92%, 93%, 94%, 95%, 96%, 97%, 98%, or 99% identical as set forth in SEQ ID NO: 4; or
a heavy chain variable domain as set forth in SEQ ID NO: 3 and/or a light chain variable domain as set forth in SEQ ID NO: 4; or
a heavy chain variable domain that is 80%, 85%, 90%, 91%, 92%, 93%, 94%, 95%, 96%, 97%, 98%, or 99%, identical to a sequence as set forth in SEQ ID NO: 5 and/or a light chain variable domain that is 80%, 85%, 90%, 91%, 92%, 93%, 94%, 95%, 96%, 97%, 98%, or 99% identical as set forth in SEQ ID NO: 4; or
a heavy chain variable domain as set forth in SEQ ID NO: 5 and/or a light chain variable domain as set forth in SEQ ID NO: 4; or
a heavy chain variable domain that is 80%, 85%, 90%, 91%, 92%, 93%, 94%, 95%, 96%, 97%, 98%, or 99%, identical to a sequence as set forth in SEQ ID NO: 6 and/or a light chain variable domain that is 80%, 85%, 90%, 91%, 92%, 93%, 94%, 95%, 96%, 97%, 98%, or 99% identical as set forth in SEQ ID NO: 7;
a heavy chain variable domain as set forth in SEQ ID NO: 6 and/or a light chain variable domain as set forth in SEQ ID NO: 7.

Antibodies OREG-203, OREG-207 and OREG-210 all recognize, as a major epitope, the sequence RTVMVNLNIHNR as shown in SEQ ID NO: 8. This newly identified sequence corresponds to residues 43 to 54 of the human IL-17A sequence, as set forth in SEQ ID NO: 1. A second epitope, the sequence RREPPHCPNSFRL (SEQ ID NO: 9), can be found in the IL-17A polypeptide as set forth in SEQ ID NO: 1 and corresponds to residues 123 to 135. This second epitope is only recognized by antibody OREG-210. In the frame of the invention, the major epitope is defined as the region of the antigen which shows the strongest binding with the tested antibody. These epitopes are the core binding regions. Adjacent regions are often also involved in giving the epitope the correct structure Another aspect of the invention concerns any IL-17 antibody having, as the major antibody binding epitopes, the same epitope as reference antibodies OREG-203, OREG-207 and OREG-210. A further aspect of the invention concerns any IL-17 antibody having, as a major antibody binding epitope, the sequence RTVMVNLNIHNR (SEQ ID NO: 8) of the human IL-17A protein formed by amino acid residues 43 to 54 of sequence SEQ ID NO: 1. A further aspect of the invention concerns any IL-17 antibody having, as a major antibody binding epitope, the sequence RREPPHCPNSFRL (SEQ ID NO: 9) of the human IL-17A protein formed by amino acid residues 123 to 135 of sequence SEQ ID NO: 1.

In another aspect, the invention is directed to an antibody that specifically binds to IL-17, more particularly human IL-17, and competitively inhibits binding of a reference antibody, wherein the reference antibody comprises:
a heavy chain variable domain as set forth in SEQ ID NO: 3 and/or a light chain variable domain as set forth in SEQ ID NO: 4;
a heavy chain variable domain as set forth in SEQ ID NO:5 and/or a light chain variable domain as set forth in SEQ ID NO: 4; or
a heavy chain variable domain as set forth in SEQ ID NO:6 and/or a light chain variable domain as set forth in SEQ ID NO: 7.

Antibodies of the invention can be produced by any technique well known in the art. In particular said antibodies are produced by techniques as hereinafter described. Polyclonal as well as monoclonal antibodies are concerned by the present invention. Monoclonal antibodies (mAb) are preferred.

In another embodiment, an antibody of the invention is a chimeric antibody, preferably a chimeric mouse/human antibody. In particular, said mouse/human chimeric antibody may comprise the variable domains of the antibodies according to the invention.

In another embodiment, an antibody of the invention is a humanized antibody. In particular, in said humanized antibody, the variable domain comprises human acceptor frameworks regions, and optionally human constant domain where present, and non-human donor CDRs, such as mouse CDRs as defined above.

In another embodiment, an antibody of the invention is a human antibody.

The invention further provides fragments of said antibodies which include but are not limited to Fv, Fab, F(ab')2, Fab', dsFv, scFv, sc(Fv)2 and diabodies; and multispecific antibodies formed from antibody fragments.

In another aspect, the invention relates to a polypeptide which has a sequence that is 80%, 85%, 90%, 91%, 92%, 93%, 94%, 95%, 96%, 97%, 98%, 99%, or 100% identical to a sequence selected from the group consisting of SEQ ID NO: 3, SEQ ID NO:4, SEQ ID NO: 5, SEQ ID NO: 6 and SEQ ID NO:7.

In another aspect, the invention relates to an isolated antibody that specifically binds to IL-17, wherein the VH of said antibody comprises a Kabat heavy chain complementarity determining region-1 (VH-CDR1) amino acid sequence identical, except for conservative amino acid substitutions, to SEQ ID NO: 15 or SEQ ID NO: 21. In a particular embodiment, the VH-CDR1 amino acid sequence is SEQ ID NO: 15 or SEQ ID NO: 21.

In another aspect, the invention relates to an isolated antibody that specifically binds to IL-17, wherein the VH of said antibody comprises a Kabat heavy chain complementarity determining region-2 (VH-CDR2) amino acid sequence identical, except for conservative amino acid substitutions, to SEQ ID NO: 16 or SEQ ID NO: 22. In a particular embodiment, the VH-CDR2 amino acid sequence is SEQ ID NO: 16 or SEQ ID NO: 22.

In another aspect, the invention relates to an isolated antibody that specifically binds to IL-17, wherein the VH of said antibody comprises a Kabat heavy chain complementarity determining region-3 (VH-CDR3) amino acid sequence identical, except conservative amino acid substitutions, to SEQ ID NO: 17 or SEQ ID NO: 23. In a particular embodiment, the VH-CDR3 amino acid sequence is SEQ ID NO: 17 or SEQ ID NO: 23.

In another aspect, the invention relates to an isolated antibody that specifically binds to IL-17, wherein the VL of said antibody comprises a Kabat light chain complementarity determining region-1 (VL-CDR1) amino acid sequence identical, except for conservative amino acid substitutions, to SEQ ID NO: 18 or SEQ ID NO: 24. In a particular embodiment, the VL-CDR1 amino acid sequence is SEQ ID NO: 18 or SEQ ID NO: 24.

In another aspect, the invention relates to an isolated antibody that specifically binds to IL-17, wherein the VL of said antibody comprises a Kabat light chain complementarity determining region-2 (VL-CDR2) amino acid sequence identical, except for conservative amino acid substitutions, to SEQ ID NO: 19 or SEQ ID NO: 25. In a particular embodiment, the VL-CDR2 amino acid sequence is SEQ ID NO: 19 or SEQ ID NO: 25.

In another aspect, the invention relates to an isolated antibody that specifically binds to IL-17, wherein the VL of said antibody comprises a Kabat light chain complementarity determining region-3 (VL-CDR3) amino acid sequence identical, except for conservative amino acid substitutions, to SEQ ID NO: 20 or SEQ ID NO: 26. In a particular embodiment, the VL-CDR3 amino acid sequence is SEQ ID NO: 20 or SEQ ID NO: 26.

In another aspect, the invention relates to an isolated antibody that specifically binds to IL-17, wherein the VH of said antibody comprises VH-CDR1, VH-CDR2, and VH-CDR3 amino acid sequences comprising:
  a) SEQ ID NOs: 15, 16, and 17, respectively; or
  b) SEQ ID NOs: 21, 22, and 23, respectively; except for conservative amino acid substitutions in one or more of said VH-CDRs.

In a particular embodiment, the VH-CDR1, VH-CDR2, and VH-CDR3 amino acid sequences are
  a) SEQ ID NOs: 15, 16, and 17, respectively; or
  b) SEQ ID NOs: 21, 22, and 23, respectively.

In another aspect, the invention relates to an isolated antibody that specifically binds to IL-17, wherein the VL of said antibody or fragment thereof comprises VL-CDR1, VL-CDR2, and VL-CDR3 amino acid sequences comprising
  a) SEQ ID NOs: 18, 19, and 20, respectively; or
  b) SEQ ID NOs: 24, 25, and 26, respectively; except for conservative amino acid substitutions in one or more of said VH-CDRs.

In a particular embodiment, the VL-CDR1, VL-CDR2, and VL-CDR3 amino acid sequences are
  a) SEQ ID NOs: 18, 19, and 20, respectively; or
  b) SEQ ID NOs: 24, 25, and 26, respectively.

In one embodiment the antibody of the invention comprises a light chain constant region selected from the group consisting of a human kappa constant region and a human lambda constant region. In another embodiment, the antibody of the invention comprises a heavy chain constant region or fragment thereof. In a more particular embodiment, the heavy chain constant region or fragment thereof is human IgG1, IgG2, IgG3, IgG4, IgM, IgA1, IgA2, IgE or IgD.

In one embodiment, the antibody of the invention is a chimeric antibody. In another embodiment, the antibody of the invention is a humanized or human antibody.

In one embodiment, the antibody of the invention is a monoclonal antibody.

In one embodiment, the antibody of the invention is an antagonist of IL-17. In a more particular embodiment, the antibody of the invention is an antagonist of the human IL-17 polypeptide. In another embodiment, the antibody of the invention has neutralizing activity against IL-17.

In one embodiment, the antibody of the invention is an antibody fragment directed against IL-17, more particularly, human IL-17. In a more particular embodiment, the fragment is selected from the group consisting of Fv, Fab, F(ab')2, Fab', dsFv, scFv, sc(Fv)2 and diabodies.

In certain embodiments, the antibodies and polypeptides of the invention can be used in an isolated (e.g., purified) form or contained in a vector, such as a membrane or lipid vesicle (e.g. a liposome).

Nucleic Acids, Vectors and Recombinant Host Cells of the Invention

A further object of the invention relates to a nucleic acid sequence encoding an antibody of the invention or a fragment thereof.

In a particular embodiment, the invention relates to a nucleic acid sequence encoding the VH domain or the VL domain of mAbs OREG-203, OREG-207 and OREG-210:

TABLE 3

Nucleic acids of VH and VL domains of mAbs OREG-203, OREG-207 and OREG-210

| MAb Domains | |
|---|---|
| VH of Ab OREG-203 | ATGGCGTGGATCTCTATCATCCTCTTCCTAGTGGCAACA GCTATAGGTGTCCACTCCCAGGCTCAGCTGCAGCAGTCT GGGGCTGAGCTGGTGAAGCCTGGGGCCTCAGTGAAGAT GTCCTGCAAGGCTTTTGGCTACACCTTCACTACCTTTCCA ATAGAGTGGATGAAGCAGAATCATGGGAAGAGCCTAGA GTGGATTGGAAATTTTCATCCTTACAATGATTATACTAA GTACAATGAAAAATTCAAGGGCAAGGCCAAATTGACTG TAGAAAAATCCTCTAGGACAGTCTACTTGGAGCTCAGCC GATTAACATCTGATGACTCTGCTGTTTATTACTGTGCAAG GGGCGCCTACTATGGTGACTACGTATCCCATACTATGGA CTTCTGGGGTCAGGGAACCTCAGTCACCGTCTCCTCA (SEQ ID NO: 10) |
| VL of Ab OREG-203 | ATGGAGACAGACACACTCCTGCTATGGGTGCTGCTGCTC TGGGTTCCAGGTTCCACAGGTAACATTGTGCTGACCCAA TCTCCAGCTTCTTTGGCTGTGTCTCTAGGGCAGAGGCC ACCATATCCTGCAGAGCCAGTGAAAGTGTTGATAGTTAT GGCAATAGTTTTATGCACTGGTACCAGCAGAAACCAGGA CAGCCACCCAAACTCCTCATCTATCTTGCATCCAACCTA GAATCTGGGGTCCCTGCCAGGTTCAGTGGCAGTGGGTCT AGGACAGACTTCACCCTCACCATTGATCCTGTGGAGGCT GATGATGCTGCAATCTATTACTGTCAGCAAAATAATGAG GATCCGCTCACGTTCGGTGCTGGGACCAAGCTGGAGCTG AAA (SEQ ID NO: 11) |
| VH of Ab OREG-207 | ATGGCGTGGATCTCTATCATCCTCTTCCTAGTGGCAACA GCTATAGGTGTCCACTCCCAGGCTCAGCTGCAGCAGTCT GGGGCTGAGCTGGTGAAGCCTGGGGCCTCAGTGAAGAT GTCCTGCAAGGCTTTTGGCTACACCTTCACTACCTTTCCA ATAGAGTGGATGAAGCAGAATCATGGGAAGAGCCTAGA GTGGATTGGAAATTTTCATCCTTACAATGATTATACTAA GTACAATGAAAAATTCAAGGGCAAGGCCAAATTGACTG TAGAAAAATCCTCTAGCACAGTCTACTTGGAGCTCAGCC GATTAACATCTGATGACTCTGCTGTTTATTACTGTGCAAG GGGCGCCTACTATGGTGACTACGTATCCCATACTATGGA CTTCTGGGGTCAGGGAACCTCAGTCACCGTCTCCTCA (SEQ ID NO: 12) |

TABLE 3-continued

Nucleic acids of VH and VL domains of mAbs
OREG-203, OREG-207 and OREG-210

| MAb Domains | |
|---|---|
| VL of Ab OREG-207 | <u>ATGGAGACAGACACACTCCTGCTATGGGTGCTGCTGCTC TGGGTTCCAGGTTCCACAGG</u>TAACATTGTGCTGACCCAA TCTCCAGCTTCTTTGGCTGTGTCTCTAGGGCAGAGGGCC ACCATATCCTGCAGAGCCAGTGAAAGTGTTGATAGTTAT GGCAATAGTTTTATGCACTGGTACCAGCAGAAACCAGGA CAGCCACCCAAACTCCTCATCTATCTTGCATCCAACCTA GAATCTGGGGTCCCTGCCAGGTTCAGTGGCAGTGGGTCT AGGACAGACTTCACCCTCACCATTGATCCTGTGGAGGCT GATGATGCTGCAATCTATTACTGTCAGCAAAATAATGAG GATCCGCTCACGTTCGGTGCTGGGACCAAGCTGGAGCTG AAA (SEQ ID NO: 11) |
| VH of Ab OREG-210 | <u>ATGGCTGTCCTGGGGCTGCTTCTCTGCCTGGTGACTTTCC CAAGCTGTGTCCTGTCC</u>CAGGTGCAGCTGAAGGAGTCAG GACCTGACCTGGTGGCGCCCTCACAGAGCCTGTCCATCA CATGCACCGTCTCAGGGTTCTCATTAACCAGCTATGGTA TACACTGGGTTCGCCAGCCTCCAGGAAAGGGTCTGGAGT GGCTGGTAGTGATATGGAGTGATGGAACCACAACCTATA ATTCAGCTCTCAAATCCAGACTGAGCATCAGCAAGGACA ACTCCAAGAGCCAAGTTTTCTTAAAAATGAACAGTCTCC AAACTGATGACACAGCCATGTACTACTGTGCCTCATCCT ATGATTACTTATATCACTATACTATGGACTACTGGGGTC AAGGAACCTCAGTCACCGTCTCCTCA (SEQ ID NO: 13) |
| VL of Ab OREG-210 | <u>ATGAAGTTGCCTGTTAGGCTGTTGGTGCTGATGTTCTGG ATTCCTGCTTCCAGCAGT</u>GATGTTGTGATGACCCAAACT CCACTCTCCCTGCCTGTCAGTCTTGGAGATCAAGCCTCC ATCTCTTGCAGATCTAGTCAGAGCCTTGTACACAGTAAT GGAAACACCTATTTTCATTGGTACCTGCAGAAGCCAGGC CAGTCTCCAAAGCTCCTGATCTACAAAGTTTCCAACCGA TTTTCTGGGGTCCCAGACAGGTTCAGTGGCAGTGGATCA GGGACAGATTTCACACTCAAGATCAGCAGAGTGGAGGC TGAGGATCTGGGAGTTTATTTCTGCTCTCAAAGTACACA TGTTCCTCTCACGTTCGGTGCTGGGACCAATCTGGAGCT GAAA (SEQ ID NO: 14) |

The sequence underlined corresponds to the leading sequence.

The Kabat CDRs of Ab OREG-203 and OREG-207 are identical and have the following nucleotide sequences:

VH-CDR1
(SEQ ID NO: 27)
ACCTTTCCAATAGAG

VH-CDR2
(SEQ ID NO: 28)
AATTTTCATCCTTACAATGATTATACTAAGTACAATGAAAAATTCAA
GGGC

VH-CDR3
(SEQ ID NO: 29)
GGCGCCTACTATGGTGACTACGTATCCCATACTATGGACTTCTGGGGTCAG
GGAACCTCAGTCACCGTCTCCTCA

VL-CDR1
(SEQ ID NO: 30)
AGAGCCAGTGAAAGTGTTGATAGTTATGGCAATAGTTTTATGCAC

VL-CDR2
(SEQ ID NO: 31)
CTTGCATCCAACCTAGAATCT

VL-CDR3
(SEQ ID NO: 32)
CAGCAAAATAATGAGGATCCGCTCACGTTCGGTGCTGGGACCAAGC
TGGAGCTGAAA

The Kabat CDRs of Ab OREG-210 have the following nucleotide sequences:

VH-CDR1
(SEQ ID NO: 33)
AGCTATGGTATACAC

VH-CDR2
(SEQ ID NO: 34)
GTGATATGGAGTGATGGAACCACAACCTATAATTCAGCTCTCAAAT
CC

VH-CDR3
(SEQ ID NO: 35)
TCCTATGATTACTTATATCACTATACTATGGACTACTGGGGTCAAGG
AACCTCAGTCACCGTCTCCTCA

VL-CDR1
(SEQ ID NO: 36)
AGATCTAGTCAGAGCCTTGTACACAGTAATGGAAACACCTATTTTC
AT

VL-CDR2
(SEQ ID NO: 37)
AAAGTTTCCAACCGATTTTCT

VL-CDR3
(SEQ ID NO: 38)
TCTCAAAGTACACATGTTCCTCTCACGTTCGGTGCTGGGACCAATCT
GGAGCTGAAA

In one aspect, the invention relates to a polynucleotide which has a sequence that is 80%, 85%, 90%, 91%, 92%, 93%, 94%, 95%, 96%, 97%, 98%, 99%, or 100% identical to a sequence selected from the group consisting of SEQ ID NO: 10, SEQ ID NO: 11, SEQ ID NO: 12, SEQ ID NO: 13 and SEQ ID NO: 14.

In another aspect, the invention relates to an isolated antibody that specifically binds to IL-17, wherein a polynucleotide encoding the VH of said antibody comprises a polynucleotide encoding a Kabat heavy chain complementarity determining region-1 (VH-CDR1) amino acid sequence identical, except for conservative amino acid substitutions, to SEQ ID NO: 15 or SEQ ID NO: 21. In a particular embodiment, the polynucleotide encodes a VH-CDR1 amino acid sequence is SEQ ID NO: 15 or SEQ ID NO: 21.

In another aspect, the invention relates to an isolated antibody that specifically binds to IL-17, wherein a polynucleotide encoding the VH of said antibody comprises a polynucleotide encoding a Kabat heavy chain complementarity determining region-2 (VH-CDR2) amino acid sequence identical, except for conservative amino acid substitutions, to SEQ ID NO: 16 or SEQ ID NO: 22. In a particular embodiment, the polynucleotide encodes a VH-CDR2 amino acid sequence is SEQ ID NO: 16 or SEQ ID NO: 22.

In another aspect, the invention relates to an isolated antibody that specifically binds to IL-17, wherein a polynucleotide encoding the VH of said antibody comprises a polynucleotide encoding a Kabat heavy chain complementarity determining region-3 (VH-CDR3) amino acid sequence identical, except for conservative amino acid substitutions, to SEQ ID NO: 17 or SEQ ID NO: 23. In a particular embodiment, the polynucleotide encodes a VH-CDR3 amino acid sequence is SEQ ID NO: 17 or SEQ ID NO: 23.

In another aspect, the invention relates to an isolated antibody that specifically binds to IL-17, wherein a polynucleotide encoding the VL of said antibody comprises a polynucleotide encoding a Kabat light chain complementarity determining region-1 (VL-CDR1) amino acid sequence identical, except for conservative amino acid substitutions, to SEQ ID NO: 18 or SEQ ID NO: 24. In a particular embodiment, the polynucleotide encodes a VL-CDR1 amino acid sequence is SEQ ID NO: 18 or SEQ ID NO: 24.

In another aspect, the invention relates to an isolated antibody that specifically binds to IL-17, wherein a polynucleotide encoding the VL of said antibody comprises a polynucleotide encoding a Kabat light chain complementarity determining region-2 (VL-CDR2) amino acid sequence identical, except for conservative amino acid substitutions, to SEQ ID NO: 19 or SEQ ID NO: 25. In a particular embodiment, the polynucleotide encodes a VL-CDR2 amino acid sequence is SEQ ID NO: 19 or SEQ ID NO: 25.

In another aspect, the invention relates to an isolated antibody that specifically binds to IL-17, wherein a polynucleotide encoding the VL of said antibody comprises a polynucleotide encoding a Kabat light chain complementarity determining region-3 (VL-CDR3) amino acid sequence identical, except for conservative amino acid substitutions, to SEQ ID NO: 20 or SEQ ID NO: 26. In a particular embodiment, the polynucleotide encodes a VL-CDR3 amino acid sequence is SEQ ID NO: 20 or SEQ ID NO: 26.

In another aspect, the invention relates to an isolated antibody that specifically binds to IL-17, wherein a polynucleotide encoding the VH of said antibody comprises a polynucleotide encoding VH-CDR1, VH-CDR2, and VH-CDR3 amino acid sequences comprising:
  a) SEQ ID NOs: 15, 16, and 17, respectively; or
  b) SEQ ID NOs: 21, 22, and 23, respectively;
except for conservative amino acid substitutions in one or more of said VH-CDRs.

In a particular embodiment, the polynucleotide encodes the VH-CDR1, VH-CDR2, and VH-CDR3 amino acid sequences of
  a) SEQ ID NOs: 15, 16, and 17, respectively; or
  b) SEQ ID NOs: 21, 22, and 23, respectively.

In another aspect, the invention relates to an isolated antibody that specifically binds to IL-17, wherein a polynucleotide encoding the VL of said antibody or fragment thereof comprises a polynucleotide encoding VL-CDR1, VL-CDR2, and VL-CDR3 amino acid sequences comprising
  a) SEQ ID NOs: 18, 19, and 20, respectively; or
  b) SEQ ID NOs: 24, 25, and 26, respectively;
except for conservative amino acid substitutions in one or more of said VL-CDRs.

In a particular embodiment, the polynucleotide encodes the VL-CDR1, VL-CDR2, and VL-CDR3 amino acid sequences of
  a) SEQ ID NOs: 18, 19, and 20, respectively; or
  b) SEQ ID NOs: 24, 25, and 26, respectively.

In one embodiment, a polynucleotide of the invention comprises a nucleic acid sequence encoding light chain constant region selected from the group consisting of a human kappa constant region and a human lambda constant region. In another embodiment, a polynucleotide of the invention comprises a nucleic acid sequence encoding a heavy chain constant region or fragment thereof. In a more particular embodiment, the heavy chain constant region or fragment thereof is human IgG1, IgG2, IgG3, IgG4, IgM, IgA1, IgA2, IgE or IgD.

A further embodiment of the invention relates to a composition comprising:
  an isolated nucleic acid encoding a heavy chain variable domain wherein said nucleic acid is 80%, 85%, 90%, 91%, 92%, 93%, 94%, 95%, 96%, 97%, 98%, 99%, or 100% identical to a sequence as set forth in SEQ ID NO: 10 and/or a light chain variable domain that is 80%, 85%, 90%, 91%, 92%, 93%, 94%, 95%, 96%, 97%, 98%, 99%, or 100% identical to a sequence as set forth in SEQ ID NO: 11; or
  an isolated nucleic acid encoding a heavy chain variable domain wherein said nucleic acid is 80%, 85%, 90%, 91%, 92%, 93%, 94%, 95%, 96%, 97%, 98%, 99%, or 100% identical to a sequence as set forth in SEQ ID NO:12 and/or a light chain variable domain that is 80%, 85%, 90%, 91%, 92%, 93%, 94%, 95%, 96%, 97%, 98%, 99%, or 100% identical to a sequence as set forth in SEQ ID NO: 11; or
  an isolated nucleic acid encoding a heavy chain variable domain wherein said nucleic acid is 80%, 85%, 90%, 91%, 92%, 93%, 94%, 95%, 96%, 97%, 98%, 99%, or 100% identical to a sequence as set forth in SEQ ID NO:13 and/or a light chain variable domain that is 80%, 85%, 90%, 91%, 92%, 93%, 94%, 95%, 96%, 97%, 98%, 99%, or 100% identical to a sequence as set forth in SEQ ID NO: 14.

Typically, said nucleic acid or polynucleotide is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T et al., *J Biochem* 101(5): 1307-10, 1987), LTR promoter and enhancer of Moloney mouse leukemia virus (Kuwana Y et al., *Biochem Biophys Res Comm.*, 149(3): 960-8, 1987), promoter (Mason J O et al., *Cell*, 41(2): 479-87, 1985) and enhancer (Gillies S D et al., *Cell*, 33(3): 717-28, 1983) of immunoglobulin H chain and the like.

Any expression vector for animal cell can be used, so long as a gene encoding the human antibody C region can be inserted and expressed. Examples of suitable vectors include pAGE107 (Miyaji H et al., *Cytotechnology*, 3(2): 133-140, 1990), pAGE103 (Mizukami T et al., *J Biochem* 101(5): 1307-10, 1987), pHSG274 (Brady G et al., *Gene*, 27(2): 223-32, 1984), pKCR (O'Hare K et al, *Proc. Natl. Acad. Sci USA*, 78(3): 1527-31. 1981), pSG1 beta d2-4-(Miyaji H et al., *Cytotechnology*, 3(2): 133-140, 1990), and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include E. coli host cells and plasmid vectors, insect host cells and Baculovirus vectors, and mammalian host cells and vectors.

Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al., *Proc Natl Acad Sci USA*, 77(7): 4216-20, 1980), rat YB2/3 HL.P2.G11.16Ag.20 cell (ATCC CRL1662, hereinafter referred to as "YB2/0 cell"), and the like.

The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the invention.

Methods of Producing Antibodies of the Invention:

Antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In particular, the invention further relates to a method of producing an antibody of the invention, which method comprises the steps consisting of: (i) culturing a transformed host cell according to the invention under conditions suitable to allow expression of said antibody; and (ii) recovering the expressed antibody.

In another particular embodiment, the method comprises the steps of:

(i) culturing the hybridoma under conditions suitable to allow expression of the corresponding antibody; and (ii) recovering the expressed antibody.

Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG 1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well known in the art (See Morrison S L. et al., *Proc Natl Acad Sci USA*, 81(21):6851-5, 1984) and patent documents U.S. Pat. No. 5,202,238; and U.S. Pat. No. 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred (Shitara K et al., *J Immunol Methods*, 167(1-2): 271-8, 1994). Examples of tandem type humanized antibody expression vector include pKANTEX93 (WO 97/10354), pEE18 and the like.

Methods for producing humanized antibodies based on conventional recombinant DNA and gene transfection techniques are well known in the art (See, e.g., Riechmann L. et al., *Nature*, 332(6162): 323-7, 1988; Neuberger M S. et al., *Nature*, 312(5995): 604-8, 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519, 596; Padlan E A, *Mol Immunol.*, 28(4-5): 489-98, 1991); Studnicka G M et al., *Protein Eng.*, 7(6): 805-14, 1994; Roguska M A. et al., *Proc Natl Acad Sci USA*, 91(3): 969-73, 1994), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with human IL-17 with a protease, papaine. Also, the Fab can be produced by inserting DNA encoding Fab of the antibody into a vector for prokaryotic expression system, or for eukaryotic expression system, and introducing the vector into a prokaryote or eucaryote (as appropriate) to express the Fab.

The F(ab')2 of the present invention can be obtained treating an antibody which specifically reacts with human IL-17 with a protease, pepsin. Also, the F(ab')2 can be produced by binding Fab' described below via a thioether bond or a disulfide bond.

The Fab' of the present invention can be obtained treating F(ab')2 which specifically reacts with human IL-17 with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see e.g., WO98/45322; WO 87/02671; U.S. Pat. No. 5,859,205; U.S. Pat. No. 5,585,089; U.S. Pat. No. 4,816,567; EP0173494).

Modification of the Antibodies of the Invention

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identity, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further object of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (*Anal Biochem,* 118(1): 131-7, 1981). Enzymatic cleavage of carbohydrate moieties on antibodies can be achieved by the use of a variety of endo- and exo-glycosidases as described by Thotakura, N R. et al. (*Methods Enzymol.,* 138: 350-9, 1987).

Another type of covalent modification of the antibody comprises linking the antibody to one of a variety of non proteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

It may be also desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fe region of the antibody. Alternatively or additionally, cysteine residue(s) may be introduced in the Fe region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron Pc. et al., *J. Exp. Med.,* 176(4): 1191-5, 1992; and Shopes B., *J. Immunol.,* 148(9): 2918-22, 1992).

Diagnostic and Therapeutic Applications of the Antibodies of the Invention:

Given the large involvement of IL-17 in various diseases, the invention also concerns the diagnostic and therapeutic uses of the present antibodies.

As they bind to human IL17, especially IL-17A (existing as a homodimer (IL-17A/A) or heterodimer (IL-17A/F)), they can be used in any immunological assay for detecting and/or quantifying IL-17, e.g. ELISA assays.

Therapeutics

Moreover, it has been demonstrated that these antibodies act as IL-17 antagonists. Therefore, they can be used in a method for treating or preventing a disease associated with an increased IL-17 expression or activity ("an IL-17-mediated disease"). Said method comprises the step of administering to a subject in need thereof an antibody of the invention. The invention further provides a therapeutic method useful for treating and preventing IL-17-mediated diseases, comprising the step of administering to a subject in need thereof an antibody of the invention.

In the context of the invention, the term "treating" or "treatment", as used herein, means reversing, alleviating, inhibiting the progress of, or preventing the disorder or condition to which such term applies, or one or more symptoms of such disorder or condition. A "therapeutically effective amount" is intended for a minimal amount of active agent (e.g., IL-17 antibodies) which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

As used herein, the term "prevention" refers to preventing the disease or condition from occurring in a subject which has not yet been diagnosed as having it.

As used herein, the term "subject" denotes a mammal, such as a rodent, a feline, a canine, and a primate. Preferably a subject according to the invention is a human.

As IL-17-mediated diseases, immune-related and inflammatory diseases include for example: systemic lupus erythematosus, arthritis, psoriatic arthritis, rheumatoid arthritis, osteoarthritis, juvenile chronic arthritis, spondyloarthropathies, systemic sclerosis, idiopathic inflammatory myopathies, Sjogren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain-Barre syndrome, amyotrophic lateral sclerosis and chronic inflammatory demyelinating polyneuropathy, hepatobiliary diseases such as infectious, autoimmune chronic active hepatitis, primary biliary cirrhosis, granulomatous hepatitis, sclerosing cholangitis, inflammatory bowel disease, colitis, Crohn's disease gluten-sensitive enteropathy, and endotoxemia, autoimmune or immune-mediated skin diseases including bullous skin diseases, erythema multiforme and atopic and contact dermatitis, psoriasis, neutrophilic dermatoses, cystic fibrosis, allergic diseases such as asthma, allergic rhinitis, food hypersensitivity and urticaria, cystic fibrosis, immunologic diseases of the lung such as eosinophilic pneumonia, idiopathic pulmonary fibrosis, adult respiratory disease (ARD), acute respiratory distress syndrome (ARDS) and inflammatory lung injury such as asthma, chronic obstructive pulmonary disease (COPD), airway hyper-responsiveness, chronic bronchitis, allergic asthma and hypersensitivity pneumonitis, transplantation associated diseases including graft and organ rejection and graft-versus-host-disease, septic shock, multiple organ failure, obesity, type 2 diabetes, non alcoholic liver cirrhosis, non alcoholic liver disease, oncology (tumor angiogenesis, primary tumors and metastases; see e.g. WO 2011/141823).

Cell proliferation disorders or cancers include for example, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

Advantageously, an IL-17-mediated disease is selected from the group consisting of autoimmune diseases (rheumatoid arthritis, Crohn's disease, multiple sclerosis, Psoriasis, Psoriatic arthritis, arthritis, uveitis, systemic Lupus erythematosus, inflammatory bowel diseases, colitis, chronic colitis, type I diabetes, diabetes), allergic diseases (type IV hypersensitivity (delayed type hypersensitivity, contact hypersensitivity), asthma, chronic obstructive pulmonary disease, atopic dermatitis, chronic allergic response, airway neutrophilia, chronic severe asthma), other immune cell mediated diseases (pulmonary fibrosis, pulmonary neutrophilia, graft versus host disease), oncology (tumor angiogenesis, primary tumors and metastases; see WO 2011/141823), osteoarthritis, vascular diseases, and atherosclerosis.

More advantageously the composition of the present invention is useful for the prevention or treatment of Rheumatoid Arthritis, Multiple Sclerosis, Systemic Lupus Erythematosus, inflammatory bowel diseases, Crohn's diseases, psoriasis, ulcerative colitis, atopic dermatitis.

More advantageously, the composition of the present invention is useful for the prevention or treatment of breast cancer, colon cancer, gastric cancer, glioma, hepatocellular carcinoma, kidney cancer, leukemia, lung cancer, lymphoma, melanoma, multiple myeloma, ovarian cancer, pancreatic cancer, prostate cancer.

Antibodies of the invention can induce cancer cell death and sensitize cells to therapeutic agents; abrogate primary tumor growth, and abrogate metastases. Hence, in one aspect, the invention is directed to a method of treating or preventing a cell proliferation disorder, said method comprising administering to said cancer cells or cells at risk for becoming cancerous an antibody of the invention. In some embodiments, the method results in targeting and/or killing the cancer cells or the cells at increased risk for becoming cancerous; increasing the effectiveness of a therapeutic agent, e.g. in treating or preventing a cell proliferation disorder; and/or preventing tumor metastasis. Advantageously, the treatment is for:

targeting and/or killing the cancer cells or the cells at increased risk for becoming cancerous;
increasing the effectiveness of a therapeutic agent, advantageously a chemotherapeutic agent; and/or
preventing or treating tumor metastasis.

In an aspect, the invention is directed to a method of increasing the effectiveness of a therapeutic agent, e.g., a chemotherapeutic agent, for killing abnormally proliferating cells in a subject having a cell proliferation disorder, said method comprising administering an amount of an antibody of the invention effective to increase the effectiveness of said therapeutic agent at a time selected from the group consisting of before, during, or after administration of said chemotherapeutic agent. In one embodiment, said chemotherapeutic agent is selected from the group consisting of: doxorubicin, paclitaxel, tamoxifen, cisplatin, vincristine, and vinblastine.

Exemplary therapeutic agents include, but are not limited to chemotherapeutic agents such as vinca alkaloids, epipodophyllotoxins, anthracycline antibiotics, actinomycin D, plicamycin, puromycin, gramicidin D, paclitaxel (Taxol™, Bristol Myers Squibb), colchicine, cytochalasin B, emetine, maytansine, and amsacrine (or "mAMSA"). The vinca alkaloid class is described in GOODMAN AND GILMAN'S THE PHARMACOLOGICAL BASIS OF THERAPEUTICS (7th ed.), (1985), pp. 1277-1280. Exemplary of vinca alkaloids are vincristine, vinblastine, and vindesine. The epipodophyllotoxin class is described, for example, in GOODMAN AND GILMAN'S THE PHARMACOLOGICAL BASIS OF THERAPEUTICS (7th ed.), (1985), pp. 1280-1281. Exemplary of epipodophyllotoxins are etoposide, etoposide orthoquinone, and teniposide. The anthracycline antibiotic class is described in GOODMAN AND GILMAN'S THE PHARMACOLOGICAL BASIS OF THERAPEUTICS (7th ed.), (1985), pp. 1283-1285. Exemplary of anthracycline antibiotics are daunorubicin, doxorubicin, mitoxantraone, and bisanthrene. Actinomycin D, also called Dactinomycin, is described, for example, in GOODMAN AND GILMAN'S THE PHARMACOLOGICAL BASIS OF THERAPEUTICS (7th ed.), (1985), pp. 1281-1283. Plicamycin, also called mithramycin, is described in Goodmand and Gilman's The Pharmacological Basis of Therapeutics (7th ed), (1985), pp. 1287-1288. Additional chemotherapeutic agents include cisplatin (Platinol™, Bristol Myers Squibb), carboplatin (Paraplatin™, Bristol Myers Squibb), mitomycin (Mutamycin™, Bristol Myers Squibb), altretamine (Hexalen™, U.S. Bioscience, Inc.), cyclophosphamide (Cytoxan™, Bristol Myers Squibb), lomustine (CCNU) (CeeNU™ Bristol Myers Squibb), carmustine (BCNU) (BiCNU™, Bristol Myers Squibb).

Exemplary chemotherapeutic agents also include aclacinomycin A, aclarubicin, acronine, acronycine, adriamycin, aldesleukin (interleukin-2), altretamine (hexamiethylmelamine), aminoglutethimide, aminoglutethimide (cytadren), aminoimidazole carboxamide, amsacrine (m-AMSA; amsidine), anastrazole (arimidex), ancitabine, anthracyline, anthramycin, asparaginase (elspar), azacitdine, azacitidine (ladakamycin), azaguanine, azaserine, azauridine, 1,1',1"-phosphinothioylidynetris aziridine, azirino(2',3':3,4)pyrrolo(1,2-a)indole-4,7-dione, BCG (theracys), BCNU, BCNU chloroethyl nitrosoureas, benzamide, 4-(bis(2-chloroethyl)amino)benzenebutanoic acid, bicalutamide, bischloroethyl nitrosourea, bleomycin (blenozane), bromodeoxyuridine, broxuridine, busulfan (myleran), carbamic acid ethyl ester, chlorambucil (leukeran), chloroethyl nitrosoureas, chorozotocin (DCNU), chromomycin A3, cis-retinoic acid, cladribine (2-chlorodeoxyadenosine; 2cda; leustatin), coformycin, cyclo leucine, cyclophosphamide anhydrous, chlorambucil, cytarabine, cytarabine, cytarabine HCl (cytosar-u), 2-deoxy-2-(((methylnitrosoamino)carbonyl)amino)-D-glucose, dacarbazine, decarbazine, decarbazine (DTIC-dome), demecolcine, dexamethasone, dianhydrogalactitol, diazooxonorleucine, diethylstilbestrol, docetaxel (taxotere), eflomithine, estramustine, estramustine phosphate sodium (emcyt), ethiodized oil, ethoglucid, ethyl carbamate, ethyl methanesulfonate, fenretinide, floxuridine, floxuridine (fudr), fludarabine (fludara), fluorouracil (5-FU), fluoxymesterone (halotestin), flutamide, flutamide (eulexin), fluxuridine, gallium nitrate (granite), gemcitabine (gemzar), genistein, 2-deoxy-2-(3-methyl-3-nitrosoureido)-D-glucopyranose, goserelin (zoladex), hexestrol, hydroxyurea (hydra), idarubicin (idamycin), ifosfagemcitabine, ifosfamide (iflex), ifosfamide with mesna (MAID), interferon, interferon alfa, interferon alfa-2a, alfa-2b, alfa-n3, interleukin-2, iobenguane, iobenguane iobenguane, irinotecan (camptosar), isotretinoin (accutane), ketoconazole, 4-(bis(2-chloroethyl)amino)-L-phenylalanine, L-serine diazoacetate, lentinan, leucovorin, leuprolide acetate (LHRH-analog), levamisole (ergamisol), mannomustine, maytansine, mechlorethamine, mechlorethamine HCl (nitrogen mustard), medroxyprogesterone acetate (provera, depo provera), megestrol acetate (menace), melengestrol acetate, melphalan (alkeran), menogaril, mercaptopurin, mercaptopurine (purinethol), mercaptopurine anhydrous, MESNA, mesna (mesne), methanesulfonic acid, ethyl ester, methotrexate (mtx; methotrexate), methyl-ccnu, mimosine, misonidazole, mithramycin, mitoantrone, mitobronitol, mitoguazone, mitolactol, mitomycin (mutamycin), mitomycin C, mitotane (o,p'-DDD; lysodren), mitoxantrone HCl (novantrone), mopidamol, N,N-bis(2-chloroethyl)tetrahydro-2H-1,3,2-oxazaphosphorin-2-amine-2-oxide, N-(1-methylethyl)-4-((2-methylhydrazino)methyl)benzamide, N-methyl-bis(2-chloroethyl)amine, nicardipine, nilutamide (nilandron), nimustine, nitracrine, nitrogen mustard, nocodazole, nogalamycin, octreotide (sandostatin), pactamycin, pegaspargase (PEGx-1), pentostatin (2'-deoxycoformycin), peplomycin, peptichemio, photophoresis, picibanil, pipobroman, podofilox, podophyllotoxin, porfiromycin, prednisone, procarbazine, procarbazine HCl (matulane), prospidium, puromycin aminonucleoside, PUVA (psoralen+ultraviolet a), pyran copolymer, rapamycin, s-azacytidine, 2,4,6-tris(1-aziridinyl)-s-triazine, semustine, showdomycin, sirolimus, streptozocin (zanosar), suramin, tamoxifen citrate (nolvadex), taxon, tegafur, tenuazonic acid, TEPA, testolactone, thio-tepa, thioguanine, thiotepa (thioplex), tilorone, topotecan, tretinoin (vesanoid), triaziquone, trichodermin, triethylene glycol diglycidyl ether, triethylenemelamine, triethylenephosphoramide, triethylenethiophosphoramide, trimetrexate (neutrexin), tris(1-aziridinyl)phosphine oxide, tris(1-aziridinyl)phosphine sulfide, tris(aziridinyl)-p-benzoquinone, tris(aziridinyl)phosphine sulfide, uracil mustard, vidarabine, vidarabine phosphate, vinorelbine, vinorelbine tartrate (navelbine), (1)-mimosine, 1-(2-chloroethyl)-3-(4-methylcyclohexyl)-1-nitrosourea, (8S-cis)-10-((3-amino-2, 3,6-trideoxy-alpha-L-lyxo-hexopyranosyl)oxy)-7,8,9,10-tetrahydro-6,8,11-trihydroxy-8-(hydroxyacetyl)-1-methoxy-5,12-naphthacenedione, 131-meta-iodobenzyl guanidine (I-131 MIBG), 5-(3,3-dimethyl-1-triazenyl)-1H-imidazole-4-carboxamide, 5-(bis(2-chloroethyl)amino)-2,4 (1H,3H)-pyrimidine dione, 2,4,6-tris(1-aziridinyl)-s-thiazine, 2,3,5-tris(1-aziridinyl)-2,5-cyclo hexadiene-1,4-dione, 2-chloro-N-(2-chloroethyl)-N-methylethanamine, N,N-bis(2-chloroethyl)tetrahydro-2H-1,3,2-oxazaphosphorin-2-amine-2-oxide, 3-deazauridine, 3-iodobenzylguanidine, 5,12-naphthacenedione, 5-azacytidine, 5-fluorouracil, (1aS, 8S,8aR,8bS)-6-amino-8-(((aminocarbonyl)oxy)methyl)-1, 1a, 2,8,8a,8b-hexahydro-8a-methoxy-5-methylazirino (2',3': 3,4)pyrrolo(1,2-a)indole-4,7-dione, 6-azauridine, 6-mercaptopurine, 8-azaguanine, and combinations thereof.

In a particular embodiment, the chemotherapeutic agent used in the methods of the present invention is doxorubicin. In another particular embodiment, the chemotherapeutic agent used in the methods of the present invention is paclitaxel.

Exemplary therapeutic agents also include, but are not limited to, radiation therapies, tyrosine kinase inhibitors (e.g., azitinib, bosutinib, cediranib, crizotinib, dasatinib, erlotinib, gefitinib, imatinib, lapatinib, neratinib, nilotinib, ruxolitinib, semaxanib, vandentanib) and therapeutic antibodies (e.g., abagovomab, abciximab, adalimumab, adecatumumab, alemtuzumab, altizumab, belimumab, bevacizumab, cetuximab, gemtuzumab, ibritumomab, inflilximab, panitumumab, rituximab, tositumomab, trastuzumab).

In another aspect, the invention is directed to a method of preventing, treating or inhibiting tumor metastases or cancer invasion in a subject having a cell proliferation disorder, said method comprising administering an amount of an antibody of the invention effective to prevent or treat tumor metastases in said subject.

In a particular embodiment, the metastases originate from a primary tumor that is from a tissue or organ selected from the group consisting of breast, bladder, liver, colon, ovary, lung, kidney, cervix, stomach, intestine, prostate, esophageal, head and neck, connective tissue, and skin. In a more particular embodiment, the metastases originate from a primary tumor that is from a tissue or organ selected from the group consisting of breast, colon, lung, ovary, esophagus, head and neck, or skin (e.g., melanoma). In a more specific embodiment, the mestastasis is from a breast tumor. In another specific embodiment, the mestastasis is from a liver tumor. Non-limiting examples of types of cancer a provided elsewhere herein, and metastases could be derived from any of these cancers that has metastatic potential.

Antibodies of the invention may be also used as an adjuvant of vaccine compositions.

The invention also relates to pharmaceutical composition comprising antibodies of the invention. Therefore, antibodies of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospho lipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The invention also provides kits comprising at least one antibody of the invention. Kits containing antibodies of the invention find use in diagnostic and therapeutic assays.

Diagnostics

Advantageously, The invention further provides a diagnostic method useful during diagnosis of IL-17-mediated diseases such as neoplastic disorders, including solid tumors, which involves measuring the expression level of IL-17 protein or transcript in tissue or other cells or body fluid from an individual and comparing the measured expression level with a standard IL-17 expression level in normal tissue or body fluid, whereby an increase in the expression level compared to the standard is indicative of a disorder.

The anti-IL-17 antibodies of the invention and antigen-binding fragments, variants, and derivatives thereof, can be used to assay IL-17 protein levels in a biological sample using classical immunohistological methods known to those of skill in the art (e.g., see Jalkanen, et al., *J. Cell. Biol.* 101:976-985 (1985); Jalkanen et al., *J. Cell Biol.* 105:3087-3096 (1987)). Other antibody-based methods useful for detecting IL-17 protein expression include immunoassays, such as the enzyme linked immunosorbent assay (ELISA), immunoprecipitation, or Western blotting. Suitable assays are described in more detail elsewhere herein.

By "assaying the expression level of IL-17 polypeptide" is intended qualitatively or quantitatively measuring or estimating the level of IL-17 polypeptide in a first biological sample either directly (e.g., by determining or estimating absolute protein level) or relatively (e.g., by comparing to the disease associated polypeptide level in a second biological sample). Preferably, IL-17 polypeptide expression level in the first biological sample is measured or estimated and compared to a standard IL-17 polypeptide level, the standard being taken from a second biological sample obtained from an individual not having the disorder or being determined by averaging levels from a population of individuals not having the disorder. As will be appreciated in the art, once the "standard" IL-17 polypeptide level is known, it can be used repeatedly as a standard for comparison.

By "biological sample" is intended any biological sample obtained from an individual, cell line, tissue culture, or other source of cells potentially expressing IL-17. Methods for obtaining tissue biopsies and body fluids from mammals are well known in the art.

The anti-IL-17 antibodies for use in the diagnostic methods described above in this section are intended to include those anti-IL-17 antibodies, or fragments, variants, or derivatives that are described in detail elsewhere herein as if they were separately listed in this section.

Immunoassays

Advantageously, Anti-IL-17 antibodies, or antigen-binding fragments, variants, or derivatives thereof of the invention may be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) CURRENT PROTOCOLS IN MOLECULAR BIOLOGY (John Wiley & Sons, Inc., NY) Vol. 1, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, (1994) Current Protocols in Molecular Biology (John Wiley & Sons, Inc., NY) Vol. 1 at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, (1994) Current Protocols in Molecular Biology (John Wiley & Sons, Inc., NY) Vol. 1 at 10.8.1.

ELISAs comprise preparing antigen, coating the well of a 96-well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, (1994) Current Protocols in Molecular Biology (John Wiley & Sons, Inc., NY) Vol. 1 at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^{3}H$ or $^{125}I$) in the presence of increasing amounts of an unlabeled second antibody.

Anti-IL-17 antibodies, or antigen-binding fragments, variants, or derivatives thereof of the invention, additionally, can be employed histologically, as in immunofluorescence, immunoelectron microscopy or non-immunological assays, for in situ detection of IL-17 protein or conserved variants or peptide fragments thereof. In situ detection may be accomplished by removing a histological specimen from a patient, and applying thereto a labeled anti-IL-17 antibody, or antigen-binding fragment, variant, or derivative thereof, preferably applied by overlaying the labeled antibody (or fragment) onto a biological sample. Through the use of such a procedure, it is possible to determine not only the presence of IL-17 protein, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays and non-immunoassays for IL-17 gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of binding to IL-17 or conserved variants or peptide fragments thereof, and detecting the bound antibody by any of a number of techniques well known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled anti-IL-17 antibody, or antigen-binding fragment, variant, or derivative thereof. The solid phase support may then be washed with the buffer a second time to remove unbound antibody. Optionally the antibody is subsequently labeled. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-IL-17 antibody, or antigen-binding fragment, variant, or derivative thereof may be determined according to well known methods. Those skilled in the art will be able to determine operative and optimal assay conditions for each determination by employing routine experimentation.

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities.

Surface plasmon resonance (SPR) as performed on BIACORE® offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE® code No. BR-1001-86; BIAtechnology Handbook, version AB (reprinted 1998), BIACORE® code No. BR-1001-84. SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIACORE® measurements monitor interactions directly as they happen. The technique is well suited to determination of kinetic parameters. Comparative affinity ranking is simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIAevaluation software provides comprehensive facilities for curve fitting using both numerical integration and global fitting algorithms. With suitable analysis of the data, separate rate and affinity constants for interaction can be obtained from simple BIACORE® investigations. The range of affinities measurable by this technique is very broad ranging from mM to pM.

Epitope specificity is an important characteristic of a monoclonal antibody. Epitope mapping with BIACORE®, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two MAbs to bind simultaneously to the same antigen. MAbs directed against separate epitopes will bind independently, whereas MAbs directed against identical or closely related epitopes will interfere with each other's binding. These binding experiments with BIACORE® are straightforward to carry out.

For example, one can use a capture molecule to bind the first Mab, followed by addition of antigen and second MAb sequentially. The sensorgrams will reveal: (1) how much of the antigen binds to first Mab, (2) to what extent the second MAb binds to the surface-attached antigen, (3) if the second MAb does not bind, whether reversing the order of the pair-wise test alters the results.

Peptide inhibition is another technique used for epitope mapping. This method can complement pair-wise antibody binding studies, and can relate functional epitopes to structural features when the primary sequence of the antigen is known. Peptides or antigen fragments are tested for inhibition of binding of different MAbs to immobilized antigen. Peptides which interfere with binding of a given MAb are assumed to be structurally related to the epitope defined by that MAb.

The anti-IL-17 antibodies for use in the immunoassays described above in this section are intended to include those anti-IL-17 antibodies, or fragments, variants, or derivatives that are described in detail elsewhere herein as if they were separately listed in this section.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

The invention will further be illustrated in view of the following examples, which are not intended to be limiting.

EXAMPLES

Figure 1:
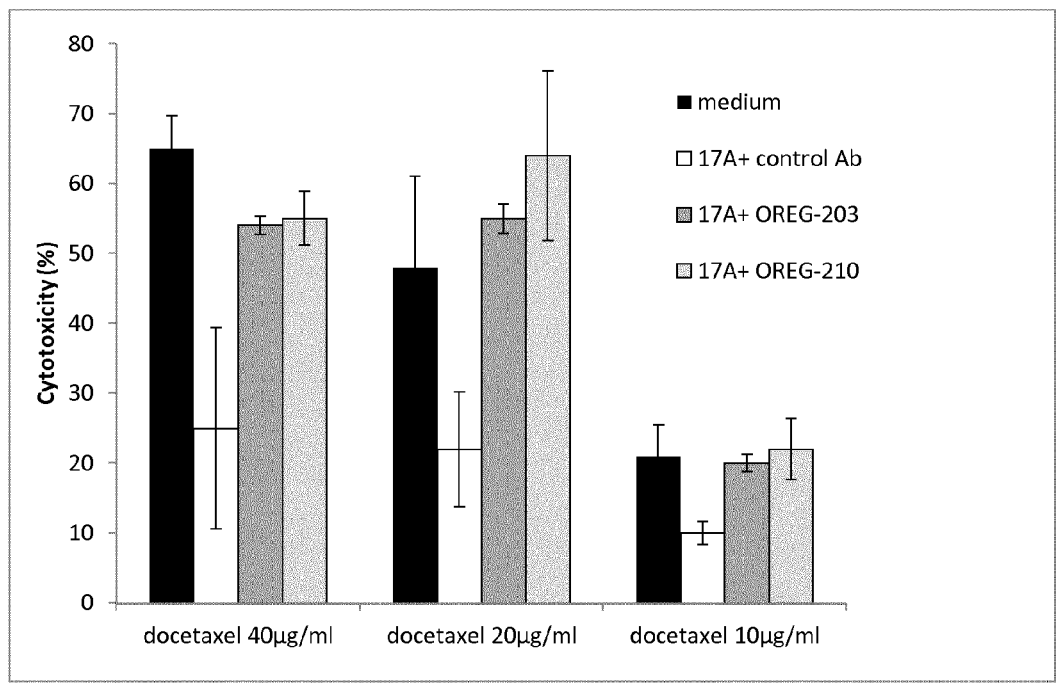
FIG. 1: Anti-IL-17A antibodies OREG-203 and OREG-210 inhibit IL-17A-induced chemoresistance in BT20 breast cancer cells. BT20 breast cancer cells were cultured in complete medium alone (medium) or supplemented with recombinant human IL-17A (10 ng/ml) and control antibody (control Ab) or anti IL-17A antibodies (OREG-203 or OREG-210) at 10 µg/ml as indicated for 48 h. Cells were then switched in FCS-free medium supplemented with IL-17A and antibodies as indicated for 24 h and then further treated with docetaxel (10 µg/ml) for 7 h. The percentage of cell death (=cytotoxicity) was determined using the Cytotoxicity Detection Kit (Roche).

Experimental Procedures:

Determination of the Affinity Constant (Ka) and the Dissociation Constant (Kd) of the Monoclonal Antibodies Against Human IL17A, Human IL17B, Human IL17C, Human IL17D, Human IL17E, Human IL17F and Human IL17A/F (Heterodimer).

First, the cross reactivity of the monoclonal antibodies towards human IL17A, human IL17B, human IL17C, human IL17D, human IL17E, human IL17F and human IL17A/F was assessed by direct ELISA. The determination of the affinity constant (Ka) and the dissociation constant (Kd) was then performed only with cytokines that demonstrated sufficient reactivity with the respective monoclonal antibody. For this determination a competitive ELISA with the various isoforms was performed. The method has been described by Friguet, B. et al. ("Measurements of the True Affinity Constant in Solution of Antigen-Antibody Complexes by Enzyme-Linked Immunosorbent Assay", J. Immunol. Methods, 77 (1985), 305-319).

The experiments were performed according to the following general ELISA protocol. All steps were performed at room temperature.

Coating with Capture Antigen (i.e. IL-17 Isoforms):

The ELISA microtest plates (96 well, 1×8 F-strips, high binding capacity, Greiner Bio-One) were coated with 50 µL/well (1 µg/ml) of the respective isoforms of IL17 in 50 mM NaHCO3, pH 9.5 coating buffer.

Antigen Used:
- recombinant human IL17A: PeproTech, Cat.-No. 200-17, Lot 040984 and Lot 1204084
- recombinant human IL17B: PeproTech, Cat.-No. 200-28, Lot 0503285-1
- recombinant human IL17C: R & D-Systems, Cat.-No. 1234-IL/CF, Lot FXJ 1111052
- recombinant human IL17D: PeproTech, Cat.-No. 200-27, Lot 0303284
- recombinant human IL17E: PeproTech, Cat.-No. 200-24, Lot 071234
- recombinant human IL17F: PeproTech, Cat.-No. 200-25, Lot 1202277
- recombinant human IL17A/F: RD systems, Cat.-No. 5194-IL/CF, Lot RXT1011102
- recombinant murine IL17A: PeproTech, Cat.-No. 210-17, Lot 1206392

Blocking

After overnight incubation, the plates were emptied and blocked with 200 µL/well TBS-TRP (50 mM Tris-HCl, 200 mM NaCl, 0.05% (v/v) Triton X-100, 0.01% (v/v) ProClin 300, 0.0004% (w/v) Phenol Red, pH 7.5) for 1 h and washed 1× with 250 µL/well TBS-TRP.

Incubation with Monoclonal Antibody a. Direct ELISA

100 µL/well of different concentrations of the monoclonal antibodies in assay buffer (50 mM Tris-HCl, 200 mM NaCl, 0.05% (v/v) Triton X-100, 1% (w/v) BSA, 0.1% (v/v) ProClin 300, pH 7.5) were added to the plates. The plates were incubated with continuous shaking and washed 4× with 250 µL/well TBS-TRP.

b. Competitive ELISA

Appropriate concentrations of the respective antigens and monoclonal antibodies were mixed in assay buffer and incubated overnight with continuous shaking at room temperature. The same monoclonal antibodies in the same concentration, but without antigen were used as positive reference (100% value). Pre-incubated antibodies were added to the plates. The plates were incubated with continuous shaking and washed 4× with 250 μL/well TBS-TRP.

Incubation with Enzyme Conjugate

100 μL/well of the enzyme conjugate (Goat-anti-mouse IgG, Fc-specific, POD Conjugate, SIGMA), finally diluted 1:60.000 in assay buffer, were added to the plates. The plates were incubated for 60 min with continuous shaking and washed 4× with 250 μL/well TBS-TRP.

Incubation with Staining Solution

The enzymatic colour reaction was obtained by adding 100 μL/well of the staining solution (TMB ONE, ready-to-use substrate, KemEnTec Diagnostics) to the plates leading to a blue product. The plates were incubated for 15 min with continuous shaking Finally the color reaction was stopped by adding directly 100 μL/well of 0.5 M sulphuric acid resulting in a yellow colored product by pH-change.

Measurement and Calculations

The optical density at 450 nm (0D450) was determined with the multichannel microplate reader OpsysMR™ (DYNEX Technologies) and the corresponding software Revelation QuickLink12 giving the raw data of the assays. For calculations and graphic presentation, the raw data were imported into the respective data files of the software GraphPad Prism™ (Version 5, © GraphPad Software Inc.).

Neutralization of the Human IL-17A and IL-17A/F Activity by the Monoclonal Antibodies The production of IL-6 in primary human normal dermal fibroblasts (NHDF) is dependent on IL-17A (Hwang S Y et al., (2004) Arthritis Res Ther; 6:R120-128).

NHDF (Lonza, CC-2511) are stimulated with 30 ng/ml (i.e., ~1 nM) recombinant IL-17A (Peprotech, 200-17) or 30 ng/ml (i.e., ~0.75 nM) recombinant IL-17A/F (RD Systems, 5194-IL/CF) in the presence of 0.5 ng/ml of TNFα (Peprotech, 300-01A) various concentrations of the antibodies. The anti-IL-17A antibody (E-biosciences, 64CAP17) was used as a positive control. An isotype control antibody was used as negative control. Supernatant is taken after 16 h stimulation and assayed for IL-6 by ELISA (Peprotech, human IL-6 development kit, cat No 900-K16).

Generation of Fragments of the Monoclonal Antibodies

Fragmentation to the monovalent Fab fragment is carried out using papain digestion and the bivalent F(ab')2 fragment is obtained by pepsin digestion, as disclosed in Current Protocols in Immunology (1997) 2.8.1-2.8.10.

Cytotoxicity Assay

Cells were seeded in a 96 wells plate (1000 cells/well) in 10% Fetal Calf Serum (FCS) adequate medium alone or treated with recombinant human IL-17A at 10 ng/ml and control antibody (D6212) or anti human IL-17A monoclonal antibodies (OREG-203 and OREG-210) at 10 μg/ml as indicated. After 48 h of culture, medium is changed to a FCS-free one supplemented with corresponding concentration of IL-17A and antibodies for 24 h as indicated. Culture medium is then further supplemented with docetaxel at 10 μg/ml. Untreated cells (control medium) and Triton X100 treated cells (100% cell death) were used as controls. Each condition was performed in duplicates.

The percentage of cell death (=cytotoxicity) was determined after 7 h of culture in the presence of docetaxel using the Cytotoxicity Detection Kit (Roche) according to the manufacturer's instructions. To this aim, 100 μl of supernatant from each well were collected into a 96 wells plate and incubated with 100 μl of freshly prepared Reaction Mixture for 30 minutes at room temperature. Optical density was then read at 490 nm. The percentage of cytotoxicity is calculated as followed: %=100×(exp value−control medium value)/(Triton X100 treated cells value−control medium value)

Migration Assay 20,000 MCF7 cells were seeded on the upper chamber of transwell chambers and cultured in RPMI medium supplemented with 1% fetal bovine serum alone (medium) or supplemented with recombinant human IL-17A (100 ng/ml), supplemented with control monoclonal antibody (D6212) or anti human IL-17A monoclonal antibodies (OREG-203 or OREG-210) as indicated (10 μg/ml), or supplemented with IL-17A (100 ng/ml) and antibodies (10 μg/ml) as indicated, for 22 hours at 37° c. The cells on the transwell were stained with 0.5% crystal violet prior imaging and enumeration. The number of cells migrated onto the transwell were counted (magnification ×4). The graph presents data after quantification in % of cell migration compared to non-treated cells. Results are the mean+/−SEM of two independent experiments, each performed in triplicate.

Results:

3 monoclonal antibodies (mAbs) directed against recombinant human IL-17 were generated in mouse, using standard protocols. They were named OREG-203, OREG-207 and OREG-210, respectively and further characterized:

Example 1

OREG-203 is a murine monoclonal $IgG_{1\kappa}$ antibody. OREG-203 binds with very high affinity to recombinant human IL-17A (Kd=714 pM, Ka=1.4 $10^9$ $M^{-1}$) and IL-17A/F (Kd=1000 pM, Ka=$10^9$ $M^{-1}$). Moreover, OREG-203 neutralizes IL-6 production induced by 1 nM recombinant human IL-17A in normal human dermal fibroblasts ($IC_{50}$=115.2 ng/ml, i.e. 0.76 nM) and neutralizes IL-6 production induced by 0.75 nM recombinant human IL-17A/F in normal human dermal fibroblasts ($IC_{50}$=30.2 ng/ml, i.e. 0.2 nM). F(ab')2 and Fab fragments of OREG-203 also neutralize IL-6 production induced by 1 nM recombinant human IL-17A in normal human dermal fibroblasts ($IC_{50}$=71.4 ng/ml, i.e. 0.714 nM and 75.9 ng/ml, i.e. 1.518 nM, respectively) and neutralize IL-6 production induced by 0.75 nM recombinant human IL-17A/F in normal human dermal fibroblasts ($IC_{50}$=27.2 ng/ml, i.e. 0.272 nM and 15.3 ng/ml, i.e. 0.306 nM, respectively).

Example 2

OREG-207 is a murine monoclonal $IgG_{1\kappa}$ antibody. OREG-207 binds with very high affinity to recombinant human IL-17A (Kd=649 pM, Ka=1.54 $10^9$ $M^{-1}$) and IL-17A/F (Kd=375 pM, Ka=2.67 $10^9$ $M^{-1}$). Moreover, OREG-207 neutralizes IL-6 production induced by 1 nM recombinant human IL-17A in normal human dermal fibroblasts ($IC_{50}$=96.5 ng/ml, i.e. 0.64 nM) and neutralizes IL-6 production induced by 0.75 nM recombinant human IL-17A/F in normal human dermal fibroblasts ($IC_{50}$=40.1 ng/ml, i.e. 0.26 nM).

Example 3

OREG-210 is a murine monoclonal $IgG_{1\kappa}$ antibody. OREG-210 binds with very high affinity to recombinant human IL-17A (Kd=1560 pM, Ka=6.4 $10^8$ $M^{-1}$) and IL-17A/F (Kd=2940 pM, Ka=3.4 $10^8$ $M^{-1}$). Moreover, OREG-210 neutralizes IL-6 production induced by 1 nM recombinant human IL-17A in normal human dermal fibroblasts ($IC_{50}$=110.3 ng/ml, i.e. 0.74 nM) and neutralizes IL-6 production induced by 0.75 nM recombinant human IL-17A/F in normal human dermal fibroblasts ($IC_{50}$=167.2 ng/ml, i.e. 1.1 nM). F(ab')2 and Fab fragments of OREG-210 also neutralize IL-6 production induced by 1 nM recombinant human IL-17A in normal human dermal fibroblasts ($IC_{50}$=1045.1 ng/ml, i.e. 10.451 nM and 1118.7 ng/ml, i.e. 22.374 nM, respectively) and neutralize IL-6 production induced by 0.75 nM recombinant human IL-17A/F in normal human dermal fibroblasts ($IC_{50}$=1159.7 ng/ml, i.e. 11.597 nM and 605 ng/ml, i.e. 12.1 nM, respectively).

Example 4

Anti-IL-17A Antibodies OREG-203 and OREG-210 Inhibit IL-17A-Induced Chemoresistance in BT20 Breast Cancer Cells As shown in FIG. 1, IL-17A protected from docetaxel-induced cytotoxicity in control antibody treated cells. Treatment with anti IL-17A antibodies OREG-203 or OREG-210 completely reverted IL-17A-mediated protection from doc-etaxel-induced cell death. Therefore, the anti IL-17A antibody OREG-203 and OREG-210 are useful to restore the sensitivity of cancer cells to chemotherapeutic agents such as docetaxel.

Example 5

Figure 2:
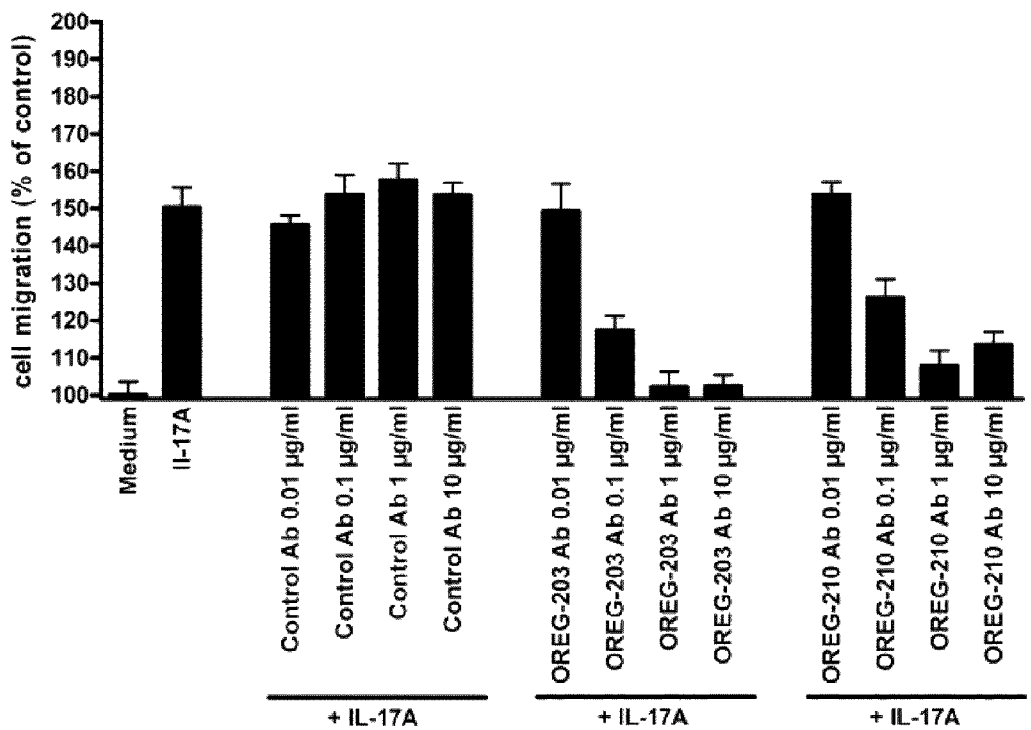
FIG. 2: Anti-IL-17A antibodies OREG-203 and OREG-210 inhibit the migration of MCF7 breast cancer cells. MCF7 cells migration was assessed in transwell chambers.

Anti-IL-17A Antibodies OREG-203 and OREG-210 Inhibit the Migration of MCF7 Breast Cancer Cells As illustrated in FIG. 2, IL-17A increased migration of MCF7 cells. The anti-IL-17A antibodies OREG-203 and OREG-210 abrogated IL-17A-induced migration in a dose dependent manner, whereas the control antibody (control Ab) had no effect. Therefore, anti-IL-17A antibodies OREG-203 and OREG-210 are useful to inhibit cancer cell migration.

The invention claimed is:

1. An isolated interleukin-17 (IL-17) antibody which binds, as a major epitope, an epitope consisting of a sequence of the human interleukin-17A (IL-17A) as set forth in SEQ ID NO: 8, the antibody comprising:
   a Kabat heavy chain complementarity determining region-1 (VH-CDR1) amino acid sequence which is identical to the VH-CDR1 of the VH region comprising the amino acid sequence as set forth in SEQ ID NO: 3 or SEQ ID NO: 5;
   a Kabat heavy chain complementarity determining region-2 (VH-CDR2) amino acid sequence which is identical to the VH-CDR2 of the VH region comprising the amino acid sequence as set forth in SEQ ID NO: 3 or SEQ ID NO: 5;
   a Kabat heavy chain complementarity determining region-3 (VH-CDR3) amino acid sequence which is identical to the VH-CDR3 of the VH region comprising the amino acid sequence as set forth in SEQ ID NO: 3 or SEQ ID NO: 5;
   a Kabat light chain complementarity determining region-1 (VL-CDR1) amino acid sequence which is identical to the VL-CDR1 of the VL region comprising the amino acid sequence as set forth in SEQ ID NO: 4;
   a Kabat light chain complementarity determining region-2 (VL-CDR2) amino acid sequence which is identical to the VL-CDR2 of the VL region comprising the amino acid sequence as set forth in SEQ ID NO: 4; and
   a Kabat light chain complementarity determining region-3 (VL-CDR3) amino acid sequence which is identical to the VL-CDR3 of the VL region comprising the amino acid sequence as set forth in SEQ ID NO: 4.

2. The antibody of claim 1 which comprises:
   a VH region comprising the amino acid sequence as set forth in SEQ ID NO: 3 or SEQ ID NO: 5; and
   a VL region comprising the amino acid sequence as set forth in SEQ ID NO: 4.

3. The antibody of claim 1 which comprises:
   a Kabat heavy chain complementarity determining region-1 (VH-CDR1) amino acid sequence which is identical to the VH-CDR1 of the VH region comprising the amino acid sequence as set forth in SEQ ID NO: 6;
   a Kabat heavy chain complementarity determining region-2 (VH-CDR2) amino acid sequence which is identical to the VH-CDR2 of the VH region comprising the amino acid sequence as set forth in SEQ ID NO: 6;
   a Kabat heavy chain complementarity determining region-3 (VH-CDR3) amino acid sequence which is identical to the VH-CDR3 of the VH region comprising the amino acid sequence as set forth in SEQ ID NO: 6;
   a Kabat light chain complementarity determining region-1 (VL-CDR1) amino acid sequence which is identical to the VL-CDR1 of the VL region comprising the amino acid sequence as set forth in SEQ ID NO: 7;
   a Kabat light chain complementarity determining region-2 (VL-CDR2) amino acid sequence which is identical to the VL-CDR2 of the VL region comprising the amino acid sequence as set forth in SEQ ID NO: 7; and
   a Kabat light chain complementarity determining region-3 (VL-CDR3) amino acid sequence which is identical to the VL-CDR3 of the VL region comprising the amino acid sequence as set forth in SEQ ID NO: 7.

4. The antibody of claim 3 which comprises:
   a VH chain comprising the amino acid sequence as set forth in SEQ ID NO: 6; and
   a VL chain comprising the amino acid sequence as set forth in SEQ ID NO: 7.

5. The antibody of claim 3 wherein the Kabat heavy chain complementarity determining region-1 (VH-CDR1) amino acid sequence consists of SEQ ID NO: 21.

6. The antibody of claim 3 wherein the Kabat heavy chain complementarity determining region-2 (VH-CDR2) amino acid sequence consists of SEQ ID NO: 22.

7. The antibody of claim 3 wherein the Kabat light chain complementarity determining region-1 (VL-CDR1) amino acid sequence consists of SEQ ID NO: 24.

8. The antibody of claim 3 wherein the Kabat light chain complementarity determining region-2 (VL-CDR2) amino acid sequence consists of SEQ ID NO: 25.

9. The antibody of claim 3 wherein the Kabat heavy chain complementarity determining region-3 (VH-CDR3) amino acid sequence consists of SEQ ID NO: 23.

10. The antibody of claim 3 wherein the Kabat light chain complementarity determining region-3 (VL-CDR3) amino acid sequence consists of SEQ ID NO: 26.

11. The antibody of claim 1, which comprises a light chain constant region selected from the group consisting of a human kappa constant region and a human lambda constant region.

12. The antibody of claim 1, which comprises a heavy chain constant region or fragment thereof.

13. The antibody of claim 12 wherein the heavy chain constant region is human IgG1, IgG2, IgG3, IgG4, IgM, IgA1, IgA2, IgE or IgD.

14. The antibody of claim 1, wherein the antibody is a chimeric antibody, a human or humanized antibody, and/or a monoclonal antibody.

15. The antibody of claim 1, wherein the antibody is an antagonist of IL-17 or wherein the antibody has neutralizing activity against IL-17.

16. The antibody of claim 1, which is an antibody fragment directed against IL-17.

17. The antibody of claim 16 wherein the antibody fragment is selected from the group consisting of Fv, Fab, F(ab')2, Fab', dsFv, scFv, sc(Fv)2 and diabodies.

18. An isolated nucleic acid comprising a sequence encoding the antibody of claim 1.

19. A vector comprising an isolated nucleic acid of claim 18.

20. A host cell comprising a vector of claim 19.

21. A host cell comprising an isolated nucleic acid sequence of claim 18.

22. A method for producing an antibody that specifically binds interleukin-17 (IL-17), comprising the steps of:
culturing a host cell of claim 21 or 20 under conditions suitable for expressing the antibody, and
recovering the antibody.

23. A composition comprising an isolated nucleic acid sequence encoding a VL region and an isolated nucleic acid encoding a VH region of the antibody of claim 1.

24. A pharmaceutical composition comprising an antibody of claim 1 and a pharmaceutically acceptable carrier.

25. A method for diagnosing or treating a patient comprising the step of administering to the patient a pharmaceutical composition of claim 24.

26. A method for diagnosing or treating a patient comprising the step of administering to the patient an antibody of claim 1.

27. The antibody of claim 1 which further binds to SEQ ID NO: 9.

28. The antibody of claim 1 wherein the Kabat heavy chain complementarity determining region-1 (VH-CDR1) amino acid sequence consists of SEQ ID NO: 15.

29. The antibody of claim 1 wherein the Kabat heavy chain complementarity determining region-2 (VH-CDR2) amino acid sequence consists of SEQ ID NO: 16.

30. The antibody of claim 1 wherein the Kabat light chain complementarity determining region-1 (VL-CDR1) amino acid sequence consists of SEQ ID NO: 18.

31. The antibody of claim 1 wherein the Kabat light chain complementarity determining region-2 (VL-CDR2) amino acid sequence consists of SEQ ID NO: 19.

32. The antibody of claim 1 wherein the Kabat heavy chain complementarity determining region-3 (VH-CDR3) amino acid sequence consists of SEQ ID NO: 17.

33. The antibody of claim 1 wherein the Kabat light chain complementarity determining region-3 (VL-CDR3) amino acid sequence consists of SEQ ID NO: 20.

* * * * *

SEQUENCE LISTING

```
<160> NUMBER OF SEQ ID NOS: 38

<210> SEQ ID NO 1
<211> LENGTH: 155
<212> TYPE: PRT
<213> ORGANISM: human

<400> SEQUENCE: 1

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
                20                  25                  30

Cys Pro Asn Ser Glu Asp Lys Asn Phe Pro Arg Thr Val Met Val Asn
            35                  40                  45

Leu Asn Ile His Asn Arg Asn Thr Asn Thr Asn Pro Lys Arg Ser Ser
        50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 2
<211> LENGTH: 163
<212> TYPE: PRT
<213> ORGANISM: human

<400> SEQUENCE: 2

Met Thr Val Lys Thr Leu His Gly Pro Ala Met Val Lys Tyr Leu Leu
1               5                   10                  15

Leu Ser Ile Leu Gly Leu Ala Phe Leu Ser Glu Ala Ala Ala Arg Lys
                20                  25                  30

Ile Pro Lys Val Gly His Thr Phe Phe Gln Lys Pro Glu Ser Cys Pro
            35                  40                  45
```

```
Pro Val Pro Gly Gly Ser Met Lys Leu Asp Ile Gly Ile Ile Asn Glu
 50                  55                  60

Asn Gln Arg Val Ser Met Ser Arg Asn Ile Glu Ser Arg Ser Thr Ser
 65                  70                  75                  80

Pro Trp Asn Tyr Thr Val Thr Trp Asp Pro Asn Arg Tyr Pro Ser Glu
                 85                  90                  95

Val Val Gln Ala Gln Cys Arg Asn Leu Gly Cys Ile Asn Ala Gln Gly
            100                 105                 110

Lys Glu Asp Ile Ser Met Asn Ser Val Pro Ile Gln Gln Glu Thr Leu
            115                 120                 125

Val Val Arg Arg Lys His Gln Gly Cys Ser Val Ser Phe Gln Leu Glu
            130                 135                 140

Lys Val Leu Val Thr Val Gly Cys Thr Cys Val Thr Pro Val Ile His
145                 150                 155                 160

His Val Gln

<210> SEQ ID NO 3
<211> LENGTH: 142
<212> TYPE: PRT
<213> ORGANISM: Mus musculus

<400> SEQUENCE: 3

Met Ala Trp Ile Ser Ile Ile Leu Phe Leu Val Ala Thr Ala Ile Gly
  1               5                  10                  15

Val His Ser Gln Ala Gln Leu Gln Gln Ser Gly Ala Glu Leu Val Lys
             20                  25                  30

Pro Gly Ala Ser Val Lys Met Ser Cys Lys Ala Phe Gly Tyr Thr Phe
         35                  40                  45

Thr Thr Phe Pro Ile Glu Trp Met Lys Gln Asn His Gly Lys Ser Leu
     50                  55                  60

Glu Trp Ile Gly Asn Phe His Pro Tyr Asn Asp Tyr Thr Lys Tyr Asn
 65                  70                  75                  80

Glu Lys Phe Lys Gly Lys Ala Lys Leu Thr Val Glu Lys Ser Ser Arg
                 85                  90                  95

Thr Val Tyr Leu Glu Leu Ser Arg Leu Thr Ser Asp Asp Ser Ala Val
            100                 105                 110

Tyr Tyr Cys Ala Arg Gly Ala Tyr Tyr Gly Asp Tyr Val Ser His Thr
            115                 120                 125

Met Asp Phe Trp Gly Gln Gly Thr Ser Val Thr Val Ser Ser
            130                 135                 140

<210> SEQ ID NO 4
<211> LENGTH: 131
<212> TYPE: PRT
<213> ORGANISM: Mus musculus

<400> SEQUENCE: 4

Met Glu Thr Asp Thr Leu Leu Leu Trp Val Leu Leu Leu Trp Val Pro
  1               5                  10                  15

Gly Ser Thr Gly Asn Ile Val Leu Thr Gln Ser Pro Ala Ser Leu Ala
             20                  25                  30

Val Ser Leu Gly Gln Arg Ala Thr Ile Ser Cys Arg Ala Ser Glu Ser
         35                  40                  45

Val Asp Ser Tyr Gly Asn Ser Phe Met His Trp Tyr Gln Gln Lys Pro
     50                  55                  60
```

```
Gly Gln Pro Pro Lys Leu Leu Ile Tyr Leu Ala Ser Asn Leu Glu Ser
 65                  70                  75                  80

Gly Val Pro Ala Arg Phe Ser Gly Ser Gly Ser Arg Thr Asp Phe Thr
                 85                  90                  95

Leu Thr Ile Asp Pro Val Glu Ala Asp Asp Ala Ala Ile Tyr Tyr Cys
            100                 105                 110

Gln Gln Asn Asn Glu Asp Pro Leu Thr Phe Gly Ala Gly Thr Lys Leu
        115                 120                 125

Glu Leu Lys
    130
```

<210> SEQ ID NO 5
<211> LENGTH: 142
<212> TYPE: PRT
<213> ORGANISM: Mus musculus

<400> SEQUENCE: 5

```
Met Ala Trp Ile Ser Ile Ile Leu Phe Leu Val Ala Thr Ala Ile Gly
 1               5                  10                  15

Val His Ser Gln Ala Gln Leu Gln Gln Ser Gly Ala Glu Leu Val Lys
             20                  25                  30

Pro Gly Ala Ser Val Lys Met Ser Cys Lys Ala Phe Gly Tyr Thr Phe
         35                  40                  45

Thr Thr Phe Pro Ile Glu Trp Met Lys Gln Asn His Gly Lys Ser Leu
     50                  55                  60

Glu Trp Ile Gly Asn Phe His Pro Tyr Asn Asp Tyr Thr Lys Tyr Asn
 65                  70                  75                  80

Glu Lys Phe Lys Gly Lys Ala Lys Leu Thr Val Glu Lys Ser Ser Ser
                 85                  90                  95

Thr Val Tyr Leu Glu Leu Ser Arg Leu Thr Ser Asp Asp Ser Ala Val
            100                 105                 110

Tyr Tyr Cys Ala Arg Gly Ala Tyr Tyr Gly Asp Tyr Val Ser His Thr
        115                 120                 125

Met Asp Phe Trp Gly Gln Gly Thr Ser Val Thr Val Ser Ser
    130                 135                 140
```

<210> SEQ ID NO 6
<211> LENGTH: 139
<212> TYPE: PRT
<213> ORGANISM: Mus musculus

<400> SEQUENCE: 6

```
Met Ala Val Leu Gly Leu Leu Leu Cys Leu Val Thr Phe Pro Ser Cys
 1               5                  10                  15

Val Leu Ser Gln Val Gln Leu Lys Glu Ser Gly Pro Asp Leu Val Ala
             20                  25                  30

Pro Ser Gln Ser Leu Ser Ile Thr Cys Thr Val Ser Gly Phe Ser Leu
         35                  40                  45

Thr Ser Tyr Gly Ile His Trp Val Arg Gln Pro Pro Gly Lys Gly Leu
     50                  55                  60

Glu Trp Leu Val Val Ile Trp Ser Asp Gly Thr Thr Thr Tyr Asn Ser
 65                  70                  75                  80

Ala Leu Lys Ser Arg Leu Ser Ile Ser Lys Asp Asn Ser Lys Ser Gln
                 85                  90                  95

Val Phe Leu Lys Met Asn Ser Leu Gln Thr Asp Asp Thr Ala Met Tyr
            100                 105                 110
```

Tyr Cys Ala Ser Ser Tyr Asp Tyr Leu Tyr His Tyr Thr Met Asp Tyr
            115                 120                 125

Trp Gly Gln Gly Thr Ser Val Thr Val Ser Ser
    130                 135

<210> SEQ ID NO 7
<211> LENGTH: 131
<212> TYPE: PRT
<213> ORGANISM: Mus musculus

<400> SEQUENCE: 7

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Phe His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Leu Thr Phe Gly Ala Gly Thr Asn Leu
        115                 120                 125

Glu Leu Lys
    130

<210> SEQ ID NO 8
<211> LENGTH: 12
<212> TYPE: PRT
<213> ORGANISM: human

<400> SEQUENCE: 8

Arg Thr Val Met Val Asn Leu Asn Ile His Asn Arg
1               5                   10

<210> SEQ ID NO 9
<211> LENGTH: 13
<212> TYPE: PRT
<213> ORGANISM: human

<400> SEQUENCE: 9

Arg Arg Glu Pro Pro His Cys Pro Asn Ser Phe Arg Leu
1               5                   10

<210> SEQ ID NO 10
<211> LENGTH: 426
<212> TYPE: DNA
<213> ORGANISM: artificial sequence
<220> FEATURE:
<223> OTHER INFORMATION: VH of Ab 203

<400> SEQUENCE: 10
atggcgtgga tctctatcat cctcttccta gtggcaacag ctataggtgt ccactcccag     60
gctcagctgc agcagtctgg ggctgagctg gtgaagcctg ggcctcagt gaagatgtcc    120 tgcaaggctt ttggctacac cttcactacc tttccaatag agtggatgaa gcagaatcat    180

```
gggaagagcc tagagtggat tggaaatttt catccttaca atgattatac taagtacaat    240
gaaaaattca agggcaaggc caaattgact gtagaaaaat cctctaggac agtctacttg    300
gagctcagcc gattaacatc tgatgactct gctgtttatt actgtgcaag gggcgcctac    360
tatggtgact acgtatccca tactatggac ttctggggtc agggaacctc agtcaccgtc    420
tcctca                                                                426

<210> SEQ ID NO 11
<211> LENGTH: 393
<212> TYPE: DNA
<213> ORGANISM: artificial sequence
<220> FEATURE:
<223> OTHER INFORMATION: VL of Ab 203 and 207

<400> SEQUENCE: 11
atggagacag acacactcct gctatgggtg ctgctgctct gggttccagg ttccacaggt     60
aacattgtgc tgacccaatc tccagcttct ttggctgtgt ctctagggca gagggccacc    120
atatcctgca gagccagtga aagtgttgat agttatggca atagttttat gcactggtac    180
cagcagaaac caggacagcc acccaaactc ctcatctatc ttgcatccaa cctagaatct    240
ggggtccctg ccaggttcag tggcagtggg tctaggacag acttcaccct caccattgat    300
cctgtggagg ctgatgatgc tgcaatctat tactgtcagc aaaataatga ggatccgctc    360
acgttcggtg ctgggaccaa gctggagctg aaa                                 393

<210> SEQ ID NO 12
<211> LENGTH: 426
<212> TYPE: DNA
<213> ORGANISM: artificial sequence
<220> FEATURE:
<223> OTHER INFORMATION: VH of Ab 207

<400> SEQUENCE: 12
atggcgtgga tctctatcat cctcttccta gtggcaacag ctataggtgt ccactcccag     60
gctcagctgc agcagtctgg ggctgagctg gtgaagcctg ggcctcagt gaagatgtcc     120 tgcaaggctt ttggctacac cttcactacc tttccaatag agtggatgaa gcagaatcat    180
gggaagagcc tagagtggat tggaaatttt catccttaca atgattatac taagtacaat    240
gaaaaattca agggcaaggc caaattgact gtagaaaaat cctctagcac agtctacttg    300
gagctcagcc gattaacatc tgatgactct gctgtttatt actgtgcaag gggcgcctac    360
tatggtgact acgtatccca tactatggac ttctggggtc agggaacctc agtcaccgtc    420
tcctca                                                                426

<210> SEQ ID NO 13
<211> LENGTH: 417
<212> TYPE: DNA
<213> ORGANISM: artificial sequence
<220> FEATURE:
<223> OTHER INFORMATION: VH of Ab 210

<400> SEQUENCE: 13
atggctgtcc tggggctgct tctctgcctg gtgactttcc caagctgtgt cctgtcccag     60
gtgcagctga aggagtcagg acctgacctg gtggcgccct cacagagcct gtccatcaca    120
tgcaccgtct cagggttctc attaaccagc tatggtatac actgggttcg ccagcctcca    180
ggaaagggtc tggagtggct ggtagtgata tggagtgatg aaccacaac ctataattca    240 gctctcaaat ccagactgag catcagcaag gacaactcca agagccaagt tttcttaaaa    300
```

-continued

```
atgaacagtc tccaaactga tgacacagcc atgtactact gtgcctcatc ctatgattac      360
ttatatcact atactatgga ctactgggggt caaggaacct cagtcaccgt ctcctca        417
```

<210> SEQ ID NO 14
<211> LENGTH: 393
<212> TYPE: DNA
<213> ORGANISM: artificial sequence
<220> FEATURE:
<223> OTHER INFORMATION: VL of Ab 210

<400> SEQUENCE: 14

```
atgaagttgc ctgttaggct gttggtgctg atgttctgga ttcctgcttc cagcagtgat       60
gttgtgatga cccaaactcc actctccctg cctgtcagtc ttggagatca agcctccatc      120
tcttgcagat ctagtcagag ccttgtacac agtaatggaa acacctattt tcattggtac      180
ctgcagaagc caggccagtc tccaaagctc ctgatctaca agtttccaa ccgatttct        240 ggggtcccag acaggttcag tgcagtgga tcaggacag atttcacact caagatcagc       300
agagtggagg ctgaggatct gggagtttat ttctgctctc aaagtacaca tgttcctctc      360
acgttcggtg ctgggaccaa tctggagctg aaa                                   393
```

<210> SEQ ID NO 15
<211> LENGTH: 5
<212> TYPE: PRT
<213> ORGANISM: artificial sequence
<220> FEATURE:
<223> OTHER INFORMATION: Ab 203 and 207 Kabat VH-CDR1

<400> SEQUENCE: 15

```
Thr Phe Pro Ile Glu
1               5
```

<210> SEQ ID NO 16
<211> LENGTH: 17
<212> TYPE: PRT
<213> ORGANISM: artificial sequence
<220> FEATURE:
<223> OTHER INFORMATION: Ab 203 and 207 Kabat VH-CDR2

<400> SEQUENCE: 16

```
Asn Phe His Pro Tyr Asn Asp Tyr Thr Lys Tyr Asn Glu Lys Phe Lys
1               5                   10                  15

Gly
```

<210> SEQ ID NO 17
<211> LENGTH: 25
<212> TYPE: PRT
<213> ORGANISM: artificial sequence
<220> FEATURE:
<223> OTHER INFORMATION: Ab 203 and 207 Kabat VH-CDR3

<400> SEQUENCE: 17

```
Gly Ala Tyr Tyr Gly Asp Tyr Val Ser His Thr Met Asp Phe Trp Gly
1               5                   10                  15

Gln Gly Thr Ser Val Thr Val Ser Ser
            20                  25
```

<210> SEQ ID NO 18
<211> LENGTH: 15
<212> TYPE: PRT
<213> ORGANISM: artificial sequence
<220> FEATURE:

<223> OTHER INFORMATION: Ab 203 and 207 Kabat VL-CDR1

<400> SEQUENCE: 18

Arg Ala Ser Glu Ser Val Asp Ser Tyr Gly Asn Ser Phe Met His
1               5                   10                  15

<210> SEQ ID NO 19
<211> LENGTH: 7
<212> TYPE: PRT
<213> ORGANISM: artificial sequence
<220> FEATURE:
<223> OTHER INFORMATION: Ab 203 and 207 Kabat VL-CDR2

<400> SEQUENCE: 19

Leu Ala Ser Asn Leu Glu Ser
1               5

<210> SEQ ID NO 20
<211> LENGTH: 19
<212> TYPE: PRT
<213> ORGANISM: artificial sequence
<220> FEATURE:
<223> OTHER INFORMATION: Ab 203 and 207 Kabat VL-CDR3

<400> SEQUENCE: 20

Gln Gln Asn Asn Glu Asp Pro Leu Thr Phe Gly Ala Gly Thr Lys Leu
1               5                   10                  15

Glu Leu Lys

<210> SEQ ID NO 21
<211> LENGTH: 5
<212> TYPE: PRT
<213> ORGANISM: artificial sequence
<220> FEATURE:
<223> OTHER INFORMATION: Ab 210 Kabat VH-CDR1

<400> SEQUENCE: 21

Ser Tyr Gly Ile His
1               5

<210> SEQ ID NO 22
<211> LENGTH: 16
<212> TYPE: PRT
<213> ORGANISM: artificial sequence
<220> FEATURE:
<223> OTHER INFORMATION: Ab 210 Kabat VH-CDR2

<400> SEQUENCE: 22

Val Ile Trp Ser Asp Gly Thr Thr Thr Tyr Asn Ser Ala Leu Lys Ser
1               5                   10                  15

<210> SEQ ID NO 23
<211> LENGTH: 23
<212> TYPE: PRT
<213> ORGANISM: artificial sequence
<220> FEATURE:
<223> OTHER INFORMATION: Ab 210 Kabat VH-CDR3

<400> SEQUENCE: 23

Ser Tyr Asp Tyr Leu Tyr His Tyr Thr Met Asp Tyr Trp Gly Gln Gly
1               5                   10                  15

Thr Ser Val Thr Val Ser Ser
            20

<210> SEQ ID NO 24

<211> LENGTH: 16
<212> TYPE: PRT
<213> ORGANISM: artificial sequence
<220> FEATURE:
<223> OTHER INFORMATION: Ab 210 Kabat VL-CDR1

<400> SEQUENCE: 24

Arg Ser Ser Gln Ser Leu Val His Ser Asn Gly Asn Thr Tyr Phe His
1               5                   10                  15

<210> SEQ ID NO 25
<211> LENGTH: 7
<212> TYPE: PRT
<213> ORGANISM: artificial sequence
<220> FEATURE:
<223> OTHER INFORMATION: Ab 210 Kabat VL-CDR2

<400> SEQUENCE: 25

Lys Val Ser Asn Arg Phe Ser
1               5

<210> SEQ ID NO 26
<211> LENGTH: 19
<212> TYPE: PRT
<213> ORGANISM: artificial sequence
<220> FEATURE:
<223> OTHER INFORMATION: Ab 210 Kabat VL-CDR3

<400> SEQUENCE: 26

Ser Gln Ser Thr His Val Pro Leu Thr Phe Gly Ala Gly Thr Asn Leu
1               5                   10                  15

Glu Leu Lys

<210> SEQ ID NO 27
<211> LENGTH: 15
<212> TYPE: DNA
<213> ORGANISM: artificial sequence
<220> FEATURE:
<223> OTHER INFORMATION: Ab 203 and 207 Kabat VH-CDR1

<400> SEQUENCE: 27
acctttccaa tagag                                                    15

<210> SEQ ID NO 28
<211> LENGTH: 51
<212> TYPE: DNA
<213> ORGANISM: artificial sequence
<220> FEATURE:
<223> OTHER INFORMATION: Ab 203 and 207 Kabat VH-CDR2

<400> SEQUENCE: 28
aattttcatc cttacaatga ttatactaag tacaatgaaa aattcaaggg c             51

<210> SEQ ID NO 29
<211> LENGTH: 75
<212> TYPE: DNA
<213> ORGANISM: artificial sequence
<220> FEATURE:
<223> OTHER INFORMATION: Ab 203 and 207 Kabat VH-CDR3

<400> SEQUENCE: 29
ggcgcctact atggtgacta cgtatcccat actatggact tctggggtca gggaacctca    60
gtcaccgtct cctca                                                    75

<210> SEQ ID NO 30

<210> SEQ ID NO 30
<211> LENGTH: 45
<212> TYPE: DNA
<213> ORGANISM: artificial sequence
<220> FEATURE:
<223> OTHER INFORMATION: Ab 203 and 207 Kabat VL-CDR1

<400> SEQUENCE: 30
agagccagtg aaagtgttga tagttatggc aatagtttta tgcac    45

<210> SEQ ID NO 31
<211> LENGTH: 21
<212> TYPE: DNA
<213> ORGANISM: artificial sequence
<220> FEATURE:
<223> OTHER INFORMATION: Ab 203 and 207 Kabat VL-CDR2

<400> SEQUENCE: 31
cttgcatcca acctagaatc t    21

<210> SEQ ID NO 32
<211> LENGTH: 57
<212> TYPE: DNA
<213> ORGANISM: artificial sequence
<220> FEATURE:
<223> OTHER INFORMATION: Ab 203 and 207 Kabat VL-CDR3

<400> SEQUENCE: 32
cagcaaaata tgaggatcc gctcacgttc ggtgctggga ccaagctgga gctgaaa    57

<210> SEQ ID NO 33
<211> LENGTH: 15
<212> TYPE: DNA
<213> ORGANISM: artificial sequence
<220> FEATURE:
<223> OTHER INFORMATION: Ab 210 Kabat VH-CDR1

<400> SEQUENCE: 33
agctatggta tacac    15

<210> SEQ ID NO 34
<211> LENGTH: 48
<212> TYPE: DNA
<213> ORGANISM: artificial sequence
<220> FEATURE:
<223> OTHER INFORMATION: Ab 210 Kabat VH-CDR2

<400> SEQUENCE: 34
gtgatatgga gtgatggaac cacaacctat aattcagctc tcaaatcc    48

<210> SEQ ID NO 35
<211> LENGTH: 69
<212> TYPE: DNA
<213> ORGANISM: artificial sequence
<220> FEATURE:
<223> OTHER INFORMATION: Ab 210 Kabat VH-CDR3

<400> SEQUENCE: 35
tcctatgatt acttatatca ctatactatg gactactggg gtcaaggaac ctcagtcacc    60
gtctcctca    69

<210> SEQ ID NO 36
<211> LENGTH: 48
<212> TYPE: DNA
<213> ORGANISM: artificial sequence
<220> FEATURE:
<223> OTHER INFORMATION: Ab 210 Kabat VL-CDR1

```
<400> SEQUENCE: 36
agatctagtc agagccttgt acacagtaat ggaaacacct attttcat          48

<210> SEQ ID NO 37
<211> LENGTH: 21
<212> TYPE: DNA
<213> ORGANISM: artificial sequence
<220> FEATURE:
<223> OTHER INFORMATION: Ab 210  Kabat VL-CDR2

<400> SEQUENCE: 37
aaagtttcca accgattttc t                                       21

<210> SEQ ID NO 38
<211> LENGTH: 57
<212> TYPE: DNA
<213> ORGANISM: artificial sequence
<220> FEATURE:
<223> OTHER INFORMATION: AB 210 Kabat VL-CDR3

<400> SEQUENCE: 38
tctcaaagta cacatgttcc tctcacgttc ggtgctggga ccaatctgga gctgaaa    57
```